(12) United States Patent
Llewelyn

(10) Patent No.: US 11,423,755 B2
(45) Date of Patent: Aug. 23, 2022

(54) SYSTEM AND METHOD FOR A DIGITAL PROOF OF VACCINE

(71) Applicant: Blue Storm Media, Inc., Redwood City, CA (US)

(72) Inventor: Gareth John Llewelyn, Hign Wycombe (GB)

(73) Assignee: Blue Storm Media, Inc., Redwood City, CA (US)

( * ) Notice: Subject to any disclaimer, the term of this patent is extended or adjusted under 35 U.S.C. 154(b) by 0 days.

(21) Appl. No.: 16/867,413

(22) Filed: May 5, 2020

(65) Prior Publication Data
US 2020/0279464 A1    Sep. 3, 2020

Related U.S. Application Data

(63) Continuation-in-part of application No. 15/645,891, filed on Jul. 10, 2017, now Pat. No. 10,783,546.
(Continued)

(51) Int. Cl.
*G06Q 30/00* (2012.01)
*G08B 21/02* (2006.01)
(Continued)

(52) U.S. Cl.
CPC ............. *G08B 21/02* (2013.01); *G06F 1/163* (2013.01); *G06F 3/14* (2013.01); *G06K 7/10366* (2013.01);
(Continued)

(58) Field of Classification Search
CPC ........ G08B 21/02; G16H 10/60; G16H 15/00; G16H 50/80; H04W 4/029; H04W 4/80;
(Continued)

(56) References Cited

U.S. PATENT DOCUMENTS 7,128,258 B1 * 10/2006 Harper ................... G16H 10/65
  235/375
7,294,379 B2    11/2007 Ko et al.
(Continued)

FOREIGN PATENT DOCUMENTS

WO    WO-2021222978 A1 * 11/2021
WO    WO-2021231377 A1 * 11/2021

OTHER PUBLICATIONS

"The covid-19 vaccine or treatment will have equitable access and an affordable price for everyone"., May 1, 2020, CE Noticias Financieras (Year: 2020).*

*Primary Examiner* — Matthew L Hamilton
(74) *Attorney, Agent, or Firm* — Patent Ventures, LLC

(57) ABSTRACT

A system and method for certification and distancing display on a user-worn badge device for infection prevention. In one embodiment, the system and method entails uploading a decrypted health token from the at least first user-networked device for displaying the "clean" health certification in a form of a color and/or symbol code on the at least first user-worn badge device; and uploading a pre-defined distancing rules for displaying at least one of color/symbol/audio-coded warning of registering presence at least a second user-worn badge device within a threshold distance of the first user-worn badge device based on the pre-defined distancing rule.

6 Claims, 22 Drawing Sheets

Related U.S. Application Data

(60) Provisional application No. 62/603,163, filed on May 17, 2017.

(51) Int. Cl.

| | |
|---|---|
| *G16H 15/00* | (2018.01) |
| *G16H 50/80* | (2018.01) |
| *G07C 9/28* | (2020.01) |
| *G07C 9/22* | (2020.01) |
| *G06F 1/16* | (2006.01) |
| *H04L 9/30* | (2006.01) |
| *G06F 3/14* | (2006.01) |
| *G09G 5/36* | (2006.01) |
| *G09G 5/02* | (2006.01) |
| *H04W 4/80* | (2018.01) |
| *H04W 4/029* | (2018.01) |
| *G06K 7/10* | (2006.01) |
| *G16H 10/60* | (2018.01) |
| *G07C 9/00* | (2020.01) |

(52) U.S. Cl.
CPC .......... *G07C 9/00571* (2013.01); *G07C 9/22* (2020.01); *G07C 9/28* (2020.01); *G09G 5/02* (2013.01); *G09G 5/36* (2013.01); *G16H 10/60* (2018.01); *G16H 15/00* (2018.01); *G16H 50/80* (2018.01); *H04L 9/30* (2013.01); *H04W 4/029* (2018.02); *H04W 4/80* (2018.02); *G09G 2354/00* (2013.01); *G09G 2380/08* (2013.01)

(58) Field of Classification Search
CPC ........ G07C 9/22; G07C 9/28; G07C 9/00571; G01F 1/163; G06F 3/14; G06K 7/10366; G09G 5/02; G09G 5/36; G09G 2354/00; G09G 2380/08
See application file for complete search history.

(56) References Cited

U.S. PATENT DOCUMENTS

| | | | |
|---|---|---|---|
| 9,715,817 B2 | 7/2017 | Wildman et al. | |
| 9,965,943 B2 | 5/2018 | Borke et al. | |
| 10,210,738 B2 | 2/2019 | Johnson, Jr. et al. | |
| 10,558,903 B2 | 2/2020 | Manci et al. | |
| 10,719,892 B2 | 7/2020 | Dyer et al. | |
| 10,803,714 B1* | 10/2020 | Khera | G08B 5/36 |
| 10,937,296 B1* | 3/2021 | Kukreja | G06K 7/10366 |
| 10,948,287 B1* | 3/2021 | Grant | G01J 5/0806 |
| 10,991,190 B1* | 4/2021 | Luthra | G16H 40/20 |
| 11,003,880 B1* | 5/2021 | Smart | G16H 50/20 |
| 11,013,472 B1* | 5/2021 | Frieder | A61B 5/4866 |
| 2011/0216931 A1* | 9/2011 | Bui | H04R 1/1091 |
| | | | 381/333 |
| 2015/0149924 A1* | 5/2015 | Tsai | G06F 1/163 |
| | | | 715/748 |
| 2015/0348498 A1* | 12/2015 | Anderson | G06Q 30/0275 |
| | | | 345/520 |
| 2016/0028947 A1* | 1/2016 | Wexler | G06F 3/017 |
| | | | 348/207.11 |
| 2017/0352119 A1* | 12/2017 | Pittman | G16H 50/80 |
| 2018/0052970 A1* | 2/2018 | Boss | G16H 50/30 |
| 2020/0279339 A1* | 9/2020 | Akutagawa | G06Q 10/1095 |
| 2021/0012869 A1* | 1/2021 | Kotlarz | G06F 16/258 |
| 2021/0058697 A1* | 2/2021 | Manning | H04R 3/00 |
| 2021/0058736 A1* | 2/2021 | Ghazzaoui | H04W 4/90 |
| 2021/0082583 A1* | 3/2021 | Ehrlich | G16H 50/80 |
| 2021/0084451 A1* | 3/2021 | Williams | H04W 4/029 |
| 2021/0202067 A1* | 7/2021 | Williams | G06N 20/00 |
| 2021/0244364 A1* | 8/2021 | Ten Kate | A61B 5/4812 |
| 2021/0304858 A1* | 9/2021 | Lacy | G16H 10/40 |
| 2021/0313026 A1* | 10/2021 | Wagner | A61B 5/0077 |
| 2021/0313069 A1* | 10/2021 | Williams | G16H 50/30 |
| 2021/0327548 A1* | 10/2021 | Sparks | G06F 21/6245 |

\* cited by examiner

Basic NVP Language

Certification Display Scheme

COVID-Free

Certification setting off=red square

COVID-Free

Certification setting on = green square

Distancing Display Legend

Contact Free

Brief Contact registered

Contact Free/Dense

Extended Contact registered

Certification Display Legend

Covid-Free           Covid-Free
tested > 2 weeks ago

Covid Vaccinated/Ab +    Covid Vaccinated/Ab +
beyond 12 months         within 12 months

Certificate Decryption/Display Pathway uploading a decrypted health token from the at least first user-networked device for displaying the "clean" health certification in a form of a color and/or symbol code on the at least first user-worn badge device 2202;

uploading a pre-defined distancing rules for displaying at least one of color/symbol/audio-coded warning of registering presence at least a second user-worn badge device within a threshold distance of the first user-worn badge device based on the pre-defined distancing rule 2204.

FIG. 22

SYSTEM AND METHOD FOR A DIGITAL PROOF OF VACCINE

RELATED U.S. APPLICATIONS DATA

This application claims priority under 35 U.S.C. 119(e) of provisional patent application No. 62/603,163 filed on May 17, 2017, entitled "Non-verbal Person to Person Line of Sight Electronic Communication Protocol Standard", which are hereby incorporated by reference in their entirety.

FIELD OF INVENTION

The present invention relates to an interactive digital badge, and more particularly, relates to a certification and distancing display on a digital badge to facilitate infection prevention.

BACKGROUND OF INVENTION

Badges have long been a mainstay in public gathering situations as a way to identify the people engaged in the public gathering. It has also been a primary way of communicating to others a level of credential to facilitate access or a professional process. While the badge has long been simply a name card, with title, and possibly a photo, they have recently morphed into digital versions. Digital badges may be operatively coupled to networked devices and be enabled to reconfigurably display items. According to one embodiment disclosed and claimed by Identity Systems, Inc. (US20150348498), the digital badge device may include a mounting means, power source, microprocessor, memory, and display to receive and display digital content from a network device according to a pre-defined rule. Identity Systems badge may be associated with an individual or employee, and then automatically display at least the name of the individual or employee based on the association and the pre-defined interaction rules between the digital badge and networked device.

Identity Systems digital badge does not disclose or claim for any digital interaction between digital badges. In other words, the badges are not configured to communicate between badges or share digital content between badges or from badge to networked device. Therefore, the badges are simply contemplated as being a visual display of identity or group/brand association—that may be dynamically displayed according to a pre-defined rule. However, it is not envisioned to serve as a true digital communication tool, that may interact with other badges, and push digital content from one badge to another badge—in a dynamic and targeted fashion. Additionally, badge-displayed content or badge-badge shared content is not enabled for social media sharing or inclusion into a running virtual footprint of a badge wearer. What's more, without tracking of such a virtual footprint, behavior or influence ratings cannot be accurately identified in order to dynamically push targeted content.

Aside from a lack of badge-badge or badge-device interactivity or footprint tracking for targeted content delivery, digital badges lack a system or protocol for communicating an approach or further engagement of digital content interaction. More specifically, badges, such as Invent Systems, lack a symbol or color-coded display cue between users who are in their 'line of sight' (or groups of people) for communicating a permission to approach, and more particularly, further sharing of content messages, emotions, feelings, wellbeing, states of mind, general interest, marketing and advertising, and interactive behavior for likeminded people.

Digital badges need a form of universal standard language which would transcend normal language and enhance it for the digital communication between at least two badges or at least between badge and receiver. The communication protocol would also need to take this language into account to enable humans to act on the language interaction. Conventionally, people cannot transmit a message directly to another person who is in their line of sight without talking, signaling or using a facial expression to communicate with them. There is currently no method for a person to send an electronic signal to person in their line of sight directly. There is currently no method for an individual to display and instantly transmit their willingness to be approached, feelings, emotions, state of mind, state of like-mindedness, social media footprint, general interests and digital information or online dashboards. Furthermore, there is no global standard or universal symbol language to communicate non-verbal approach messages via badge devices. Currently, there is also no way for two like-minded people to share non-verbal content messages between badges and, or static devices.

In the midst of the Coronavirus pandemic gripping the entire world, it has become increasingly clear that a line-of-sight signaling devise may be crucial for signaling to others a "health status". This displayed "health status" would ensure an "up-to-the-minute" digital certification issued by a public health registry—allaying any concerns or fears from others attempting to engage. This "health status" display would allow for even non-essential channels of commerce to reopen. It has been recently estimated by the IMF that we will experience a 3% contraction in global GDP as a result of the pandemic. The sectors that have been most affected are those that involve a high-level of social interaction, such as the food service industry. According to a recent report from the National Restaurant Association, 3% of the 4,000 member restaurants have already permanently gone out of business, with a staggering 12% anticipating going out of business by the end of April 2020. This vital channel of commerce may be reopened—despite the lack of ubiquitous testing or a vaccine—provided every customer and employee was mandated to display a time-stamped public health agency-issued "COVID-free" certification.

Furthermore, there is sorely a need for a user-worn display device that may also be used as a social distancing and contact tracing tool. While there is an emerging consensus that social distancing has been instrumental in flattening the epidemiological curve, in reality, it is quite difficult to constantly practice, especially in more dense cities, such as New York City. Practicing social distancing in heavily foot-trafficked scenarios would be significantly easier with a device triggering a color, symbol, or audio alert upon detecting the presence of another device within a threshold proximity. Moreover, this registered contact could be tracked for facilitating future contact tracing efforts. While there are a number of apps designed to track contact for tracing purposes (TraceTogether), the contact registered is not made known to the individuals involved at the time of contact. The extant systems are mobile device-based and do not feature a line-of-sight display alerting individuals of the contact at the time of the contact. Without a line-of-sight real-time alert, individuals may be prone to unwittingly extending the contact, thereby further exposing oneself to an infection.

SUMMARY

The non-verbal line of sight electronic communication protocol (NVP) described herein allows the viewer to instantly understand the symbol and, or color-coded display cues of the interactive badge and understand whether the individual displaying the visual cues can be: (1) approached and (2) whether an information exchange can take place immediately or in the future. It also allows the user to send and receive information that could not previously be exchanged through normal human communication means.

Generally, the non-verbal line of sight electronic communication protocol (NVP) includes a standardized set of symbols, colors, and electronic communication protocol standards that enhance human communication to a new level. The NVP allows individuals to create new human behaviors and send messages beyond the natural 5 senses. The NVP allows individuals to build their own window of their life, display it on a personal digital display, and then have others interact with them. The NVP allows individuals to 'think' by creating their life window, 'act' by uploading to their personal digital display, and 'do' by using the interactive communication protocol.

The NVP allows communication between humans to take place while in their line of sight over and above their normal senses. The NVP can be implemented on any personal digital display that is running the NVP protocol. This protocol allows a signal to be passed between NVP devices only when certain combination of symbols and colors are displayed. This communication can trigger the transfer of information from one individual to another. Preferably, this NVP interaction guided by the standardized set of symbols and, or colors may be displayed on a center and, or surround visual display of an interactive badge worn by a first user, and in the line of sight by at least a second user.

It is one object of the invention to disclose a non-verbal line of sight electronic communication (NVP) system, comprising an interactive badge device with a line of sight device visual display. The device visual display being at least one of a surround device display and, or a center device display. Additionally, the device may have an interface module housed within the interactive badge device and configured for causing an event state change between at least one of a mobile device, surround device display and, or center device display. Moreover, the system may have a processor; a non-transitory storage element coupled to the processor; and encoded instructions stored in the non-transitory storage element, wherein the encoded instructions when implemented by the processor, configure the system to: (1) upload NVP interaction rules and curated NVP content for display on any one of a first user's device based on the first user's interaction rules and scheduler criteria; (2) send at least one of an interaction and, or content message based on the first user's interaction rules and scheduler criteria to at least one of a second user's device within range and contingent on the second user's interaction rules; and (3) based on the second user's interaction rules, accept or deny the first user interaction message, and if accepted, decode a unique tag to trigger a unique digital event, wherein the digital event may be at least one of an image, video, sound, vibration, flash, signal, symbol, color, text, upload, sequence, download on any one of the user's device visual display, and, or over a network.

It is another object of the invention to disclose a non-verbal line of sight electronic communication protocol. The communication protocol comprising a non-verbal symbol language for communicating wirelessly over electronic devices, including interactive badges and, or displays, between users and, or static receivers, who are in one another's line of sight; and the symbol language displayed on the interactive badge and, or display and, or static receivers communicate whether a first user can approach at least a second user or not for further digital interaction.

It is yet another object of the invention to provide for a device-centric, non-verbal line of sight electronic communication protocol. The device-centric, non-verbal line of sight electronic communication protocol comprising a non-verbal symbol language for communicating wirelessly over electronic devices, including an interactive badge with a line of sight device visual display, between users who are in one another's line of sight. The symbol language further comprising a set of any shaped and, or colored symbols that are programmably displayed on the device visual display, wherein the device visual display is at least one of a surround device display and, or a center device display. Furthermore, based on the programmably displayed set of shaped and, or colored symbols on the device visual display, communicate whether a first user can approach at least a second user or not for further digital interaction.

Aspects and advantages of this invention may be realized in other applications, aside from the intended application of interactive badge device-mediated communication and a communication protocol thereof. Other pertinent applications that may exploit the aspects and advantages of this invention are: digital advertising and digital commerce platforms integrated into the NVP communication system and protocol. For instance, an activity footprint of a user's displayed NVP content and, or replicated digital or virtual NVP content may be tracked for advertisers to target the most influential users for a brand display-for-hire. Moreover, a plurality of advertisers may bid for the most influential user's using a bidding module within the advertising platform, creating upward pressure on the brand display-for-hire fees. What's more, tracking of a user's NVP line of content displayed or virtually replicated, may enable a commerce platform or participants of the platform to push suggested digital content that is personalized to the user based on the user's running NVP content. Yet another digital event that may be triggered: may be the interaction of the badge device with other badge devices or fixed access devices near access-gates, wherein the symbol and, or color-coded display on badge or fixed-access devices invite for approach; once approached and interacted with, uploading an authentication tag over a network to a remote server; validating the authentication tag against a library of authenticated tags; downloading the validated tag and using the symbol and color-coded display on the badge device or fixed-access device to communicate permission to access. Additional digital events may include enabling the same interactive badge devices or fixed-access devices to process payment transactions, over a network, via an intermediary payment system.

In another aspect, a system, method, and device for a line-of-sight user-worn digital badge device for health certification and distancing display is disclosed. The system may comprise a first user-worn display device; a first user-networked device; said first user-worn display device housing an interface to communicate with the first user-networked device and at least a second user-worn display device; said first user-worn display device comprising at least one of a front or side wall with a visual display, wherein said visual display is in a line of sight of at least a second user while worn by a first user; a key unique to any one of the user-worn display device for decrypting an encrypted health token from a public heath server via a network to the at least first user-networked device for displaying a "clean" health certification in a form of a color and/or symbol code on the at least first user-worn display device; a processor, non-transitory storage element coupled to the processor, and encoded instructions stored in the non-transitory storage element, wherein the encoded instructions when implemented by the processor, configure the system to: upload decrypted health token from the at least first user-networked device for displaying the "clean" health certification in a form of a color, symbol, and/or audio-code on the at least first user-worn display device; and upload pre-defined distancing rules from the at least first user-networked device for display on the at least first user-worn display device of at least one of color/symbol/audio-coded warning of registering presence of at least the second user-worn display device within a threshold distance of the first user-worn display device based on the pre-defined distancing rule.

Other aspects and advantages of the invention will be apparent from the following description and the appended claims.

BRIEF DESCRIPTION OF FIGURES

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which: [0016] [019]

FIG. 22 illustrates an exemplary method flow diagram for certification in accordance to an aspect of the invention.

DETAILED DESCRIPTION

In the following description, for purposes of explanation, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Overview:

The present disclosure relates to a new non-verbal language that has been developed for the emerging electronic line of sight badge communication. The language will be referred to in the document as NVP which an abbreviation of Non Verbal person to person line of sight communication protocol standard. NVP is both a language and a communication protocol and this document initially describes both and then gives examples of how this is programmed and then examples or actual uses in the identified markets.

Exemplary Environment

Figure 1:
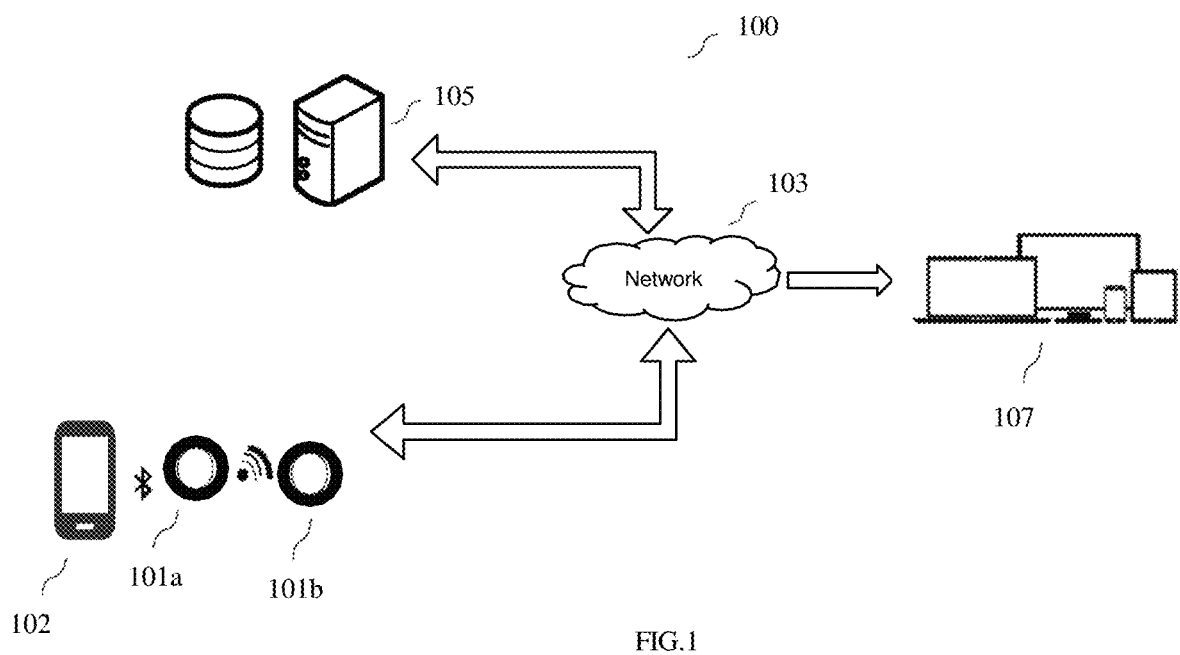
FIG. 1 illustrates a network diagram of the NVP communication system in accordance with an aspect of the invention.

Now in reference to FIG. 1. FIG. 1 illustrates an exemplary system environment 100 in which various embodiments of the non-verbal line of sight communication protocol system (NVP) can be practiced. In accordance with an exemplary embodiment, the NVP system 100 comprises: an interactive badge device 101a, 101b with a line of sight device visual display; the device visual display being at least one of a surround device display and, or a center device display; a processor; a non-transitory storage element coupled to the processor; encoded instructions stored in the non-transitory storage element, wherein the encoded instructions when implemented by the processor, configure the system 100 to: upload NVP interaction rules and curated NVP content for display on any one of a first user's interactive badge device 101a based on the first user's interaction rules and scheduler criteria; send at least one of an interaction and, or content message based on the first user's interaction rules and scheduler criteria to at least one of a second user's interactive badge device 101b within range and contingent on the second user's interaction rules; and based on the second user's interaction rules, accept or deny the first user interaction message, and if accepted, decode a unique tag to trigger a unique digital event, wherein the digital event may be at least one of an image, video, sound, vibration, flash, signal, symbol, color, text, sequence, upload, download on any one of the user's device visual display and, or over a network.

The network 103 may be any suitable wired network, wireless network, a combination of these or any other conventional network, without limiting the scope of the present invention. Few examples may include a LAN or wireless LAN connection, an Internet connection, a point-topoint connection, or other network connection and combinations thereof. The network 103 may be any other type of network that is capable of transmitting or receiving data to/from host computers, personal devices, telephones, video/image capturing devices, video/image servers, or any other electronic devices. Further, the network 103 is capable of transmitting/sending data between the mentioned devices. Additionally, the network 103 may be a local, regional, or global communication network, for example, an enterprise telecommunication network, the Internet, a global mobile communication network, or any combination of similar networks. The network 103 may be a combination of an enterprise network (or the Internet) and a cellular network, in which case, suitable systems and methods are employed to seamlessly communicate between the two networks. In such cases, a mobile switching gateway may be utilized to communicate with a computer network gateway to pass data between the two networks. The network 103 may include any software, hardware, or computer applications that can provide a medium to exchange signals or data in any of the formats known in the art, related art, or developed later.

In a preferred embodiment, the line of sight interactive digital badge device (badge device) 101a, 101b is worn on one or more body parts of the user, such as chest, wrist, waist, neck, arm, leg, abdomen, thigh, head, etc. Further, the badge device 101a, 101b may be a wristband, a watch, an armband, a necklace, a headband, an earring, a waist belt and, or a ring. Alternatively, the badge device may be any reconfigurable display that may be temporarily or permanently affixed onto a garment of a user. In yet other alternative embodiments, the reconfigurable display may be a flexible OLED tube or screen interwoven into the fabric of the garment. Badge devices 101a, 101b may have a device visual display that is situated in any one of a person's line of sight. The device visual display may be a single center display, wherein the symbol and, or color-coded visual display cueing a permission to approach and further interact is displayed on the single, center visual display. The same single, center visual display may also display the NVP content. The same display may also be enabled for touch-screen interactivity. In other embodiments, interaction with the display contents may be controlled by controls disposed on a side, top, or bottom wall of a (circular or square) device casing. In yet other embodiments, the device visual display may be comprised of a dual display: a center device display and a surround device display. Each display sharing display functions or having unique display functions. For instance, in some embodiments, the surround device display may display the symbol and, or color-coded visual cues encoding for a permission to approach and interact, while the center device display may strictly display the actual NVP content (a static or a rolling line of user-content images).

In some embodiments of the badge device 101a, 101b, sensors may be disposed within the (domed) device housing, or on the (circular or square) device casing, to capture at least one of a user environmental or contextual data to further inform a user mood, emotion, physical condition, mental well-being, and, or willingness to be approached by other digital badge users for further interaction. The digital badge device 101a, 101b is first sent to the mobile communication device 102 and thereby, sent to the processing unit over the network 103. The digital badge device 101a, 101b communicates with the mobile communication device 102 over a short-range wireless communication medium, such as Bluetooth, etc. In other embodiments, sensor input may be derived from devices other than the badge device 101a, 101b. Device input may also encompass the sensor-captured raw data input or transduced and processed data input from any other device associated with the user, such as devices worn, mobile devices, and, or fixed-access devices, such as Internet-of-Things devices (e.g. smart thermostat, home automation consoles, etc.). The plurality of device inputs provides additional input for aggregation and behavior profiling, thus layering the behavior profile with additional context for generating a higher fidelity of user mood, emotion, well-being, etc. This higher resolution of user profiling may update the user interaction rules and, or policy for determining access for approach and activating further digital event/content interaction.

In continuing reference to FIG. 1 and the exemplary environment of the NVP system, a mobile communication device 102, such as a smart phone, is a portable device that has the capability of communicating over the network 103, presenting dashboard provisioning based on a respective digital badge device 101a, 101b pairing. Examples of the mobile communication device 102 include, but are not limited to, a smartphone, a tablet, a personal digital assistant (PDA) and a mobile phone. The mobile communication device 102 may be paired with a respective digital badge device 101a, 101b over a short-range wireless communication medium.

Examples of the short-range wireless communication medium include Bluetooth, ZigBee, Infrared, Near Field Communication (NFC) and, or Radio-frequency identification (RFID). Likewise, the digital badge device 101a, 101b may interact with other digital badge devices 101a, 101b using a short-range communication protocol, such as Infrared, Bluetooth, ZigBee, NFC, and, or RFID.

Preferred embodiments may include the addition of a remote server 105 or cloud server to further provide for back-end functionality and support. The server 105 may be situated adjacent or remotely from the system 100 and connected to each system 100 via a communication network 103. In one embodiment, the server 105 may be used to support user behavior profiling; user history function; predictive learning/analytics; alert function; network sharing function; digital footprint tracking; e-commerce/advertising platform support, etc. The remote server 105 may be further configured to authenticate the user and retrieve data of the user, device, and, or network and applies the data against a library of validated user information for enabling a payment or ticket transaction at a fixed-access point deploying an embodiment of the interactive badge device 101a, 101b.

Figure 2:
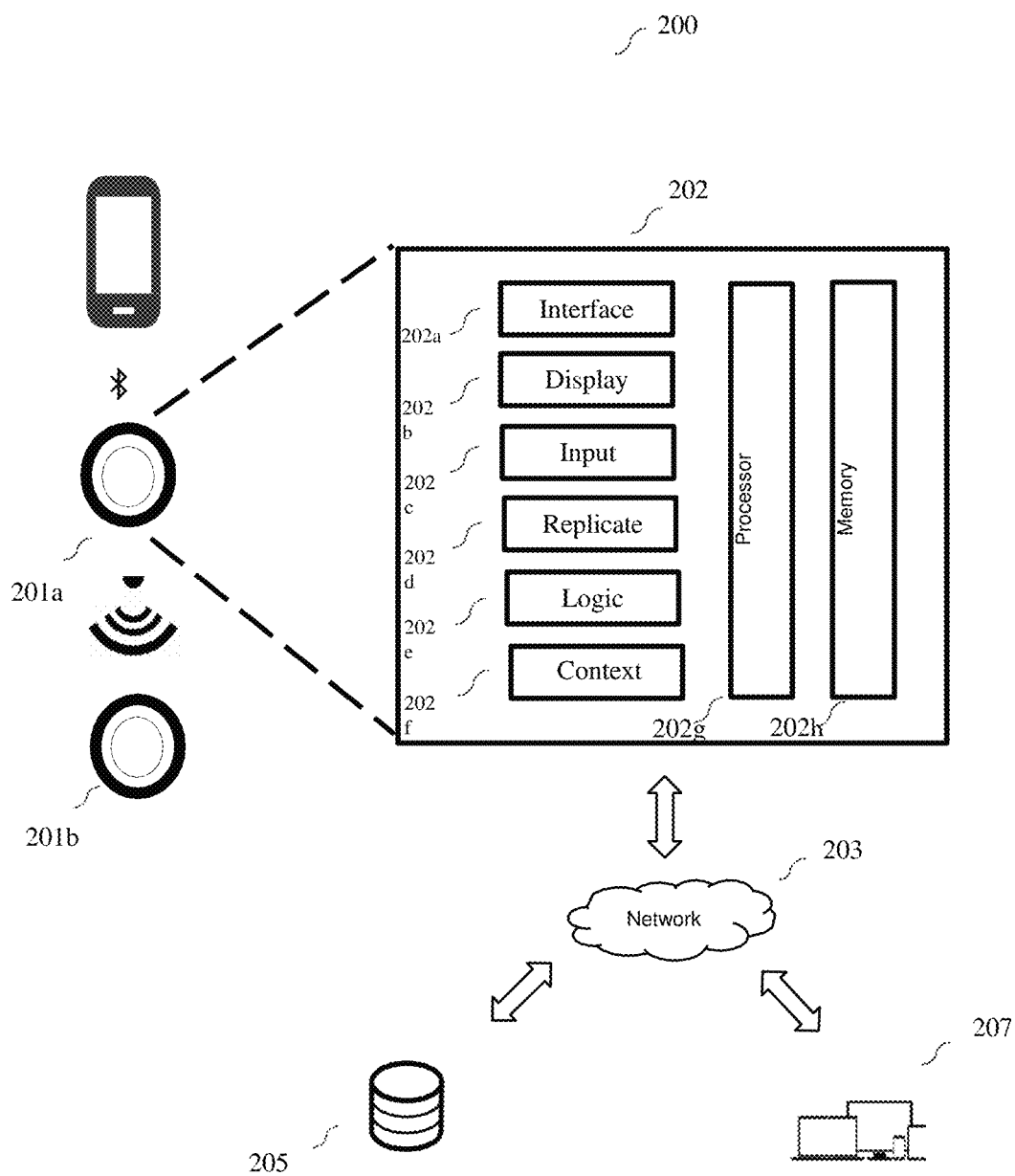
FIG. 2 illustrates a block diagram of the NVP communication system in accordance with an aspect of the invention.
Figure 3:
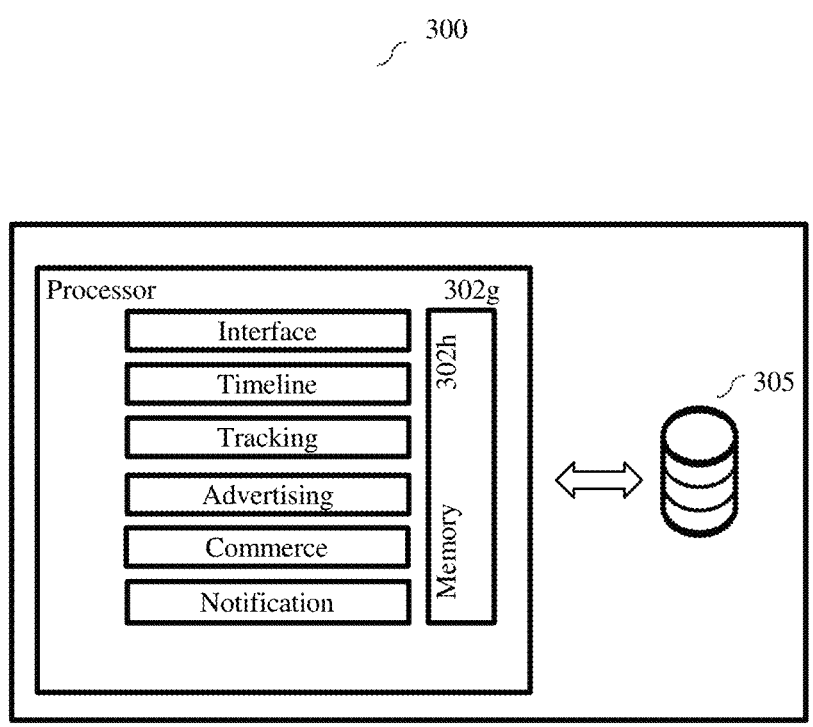
FIG. 3 illustrates a block diagram of the NVP communication system in accordance with an aspect of the invention.

Now in reference to FIGS. 2 and 3. FIGS. 2 and 3 both illustrate an exemplary embodiment of the NVP system. FIGS. 2 and 3 illustrate an exemplary processing unit 202g, 302g used for displaying a visual cue for permission to approach and, or a content display for exchange between interactive badge devices 201a, 201b or sharing over a network 203. As shown, the processing unit 202g, 302g may be communicatively coupled to at least one of an interface module 202a, display module 202b, input module 202c, replicate module 202d, a logic module 202e, a context module 202f, an interface module, a timeline module, a tracking module, 10 an advertising module, a notification module, and a commerce module. The processor 202g, 302g may also communicatively coupled to a remote database 205, 305 and a memory 202h, 302hIn an embodiment of the present invention, the processor 202g, 302g includes a notification/alerting module. The notification/alerting module is configured to generate reports at regular intervals (such as daily at 12:00 PM, weekly and monthly), on-demand (when the user requests for a report corresponding to the user), or when triggered by a digital event. Typically, a digital event may be defined as any digital display for badge-badge display or network sharing or server authentication. The notification/alerting module may double up as a tracking module, wherein a user may keep track of his or her physical displays and interactions, as well as his or her virtual displays and interactions.

In an embodiment of the present invention, the notification/alerting module may also be configured to send a notification to the user of the growing social influence of a user. In other words, an influence metric may be pushed quantifying how may people I have interacted with, and how many times my virtual NVP line of content been shared with other users on social media. The notification may be a message, a phone call or any other communication means.

In an embodiment of the present invention, the processor 202g, 302g includes a timeline module. The NVP line of content may be displayed or pushed in at least one of a static, dynamic, and, or scheduled fashion on at least one of the user's center device display based on at least one of the user's scheduler criteria. The line of static, dynamic, and, or scheduled images and, or video NVP content from at least one of the user's to be displayed on at least one of the user's center device display may be curated by the user, pre-set, or dynamically pushed based on any one of user parameter. In some embodiments, the timeline module enables the displayed line of static, dynamic, and, or scheduled images and, or video NVP content to be further replicated on at least one of a digital and, or virtual presence of at least one the users. In other words, the timeline module enables the displayed line of NVP content to be further shared with social media and digital media outlets, over a network. In some embodiments, an Application Programming Interface may be integrated and configured for enabling transfer and, or further interaction of the replicated line of static, dynamic, and, or scheduled images and, or video NVP content.

The processor 202g, 302g may include an advertising module and, or a commerce module, enabling advertisers to target users for NVP content display based on NVP activity or influence of said users. The advertising module may further comprise a bidding module, wherein the advertisers bid among each other for engaging a user for incorporating a winning bid advertisement into the NVP content display of the user. The processor 202g, 302g may further comprise a commerce module, wherein users may purchase digital downloads of NVP content for NVP content display. The commerce module may further be coupled to a distributive digital ledger, wherein each NVP exchange among any user is represented as a unique node in the digital ledger. Each node tagged with meta data facilitating at least one of a transaction, validation and, or registration for each NVP exchange.

In some embodiments, any one of the processor functioning mentioned above may be off-loaded to the processor of the mobile device and, or the remote server. The device display may simply be used for display function—for both symbol and color-coded display cues on any one of the surround display and, or center display, and NVP line of content on the center display. Exemplary Communication Protocol The NVP language is made up of symbols, shapes, colors and images that when combined form a language specifically for the person to person or groups of people interactive badge or screen market. This language is the only language that allows individuals to communicate with the interactive badge in a visual sense. The NVP may be displayed on a surrounding of the interactive badge device and, or on device center display. In some embodiments, the surround display and center display may be combined in unison, or in a sequential manner, to express the NVP language.

The NVP Language Components

Figure 4:
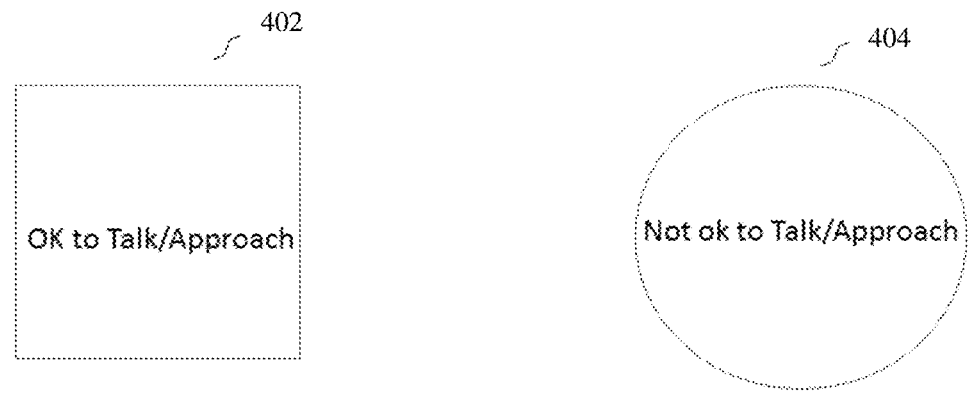
FIG. 4 illustrates a symbol and, or color-coded NVP communication protocol in accordance with an aspect of the invention.

The first component of the language is a shape such as but not limited to a square, circle, triangle or star. These shapes indicate to the viewer a behavioral welcoming state of the person viewing them. One such behavioral state might be a welcome to communicate or not as the case might be. An example of these shapes and their uses are shown in FIG. 4. This first component forms the frame of all the communication symbols to follow. It is programmed by the NVP wearer at the start of a badges or screen or display wearing session.

Figure 5:
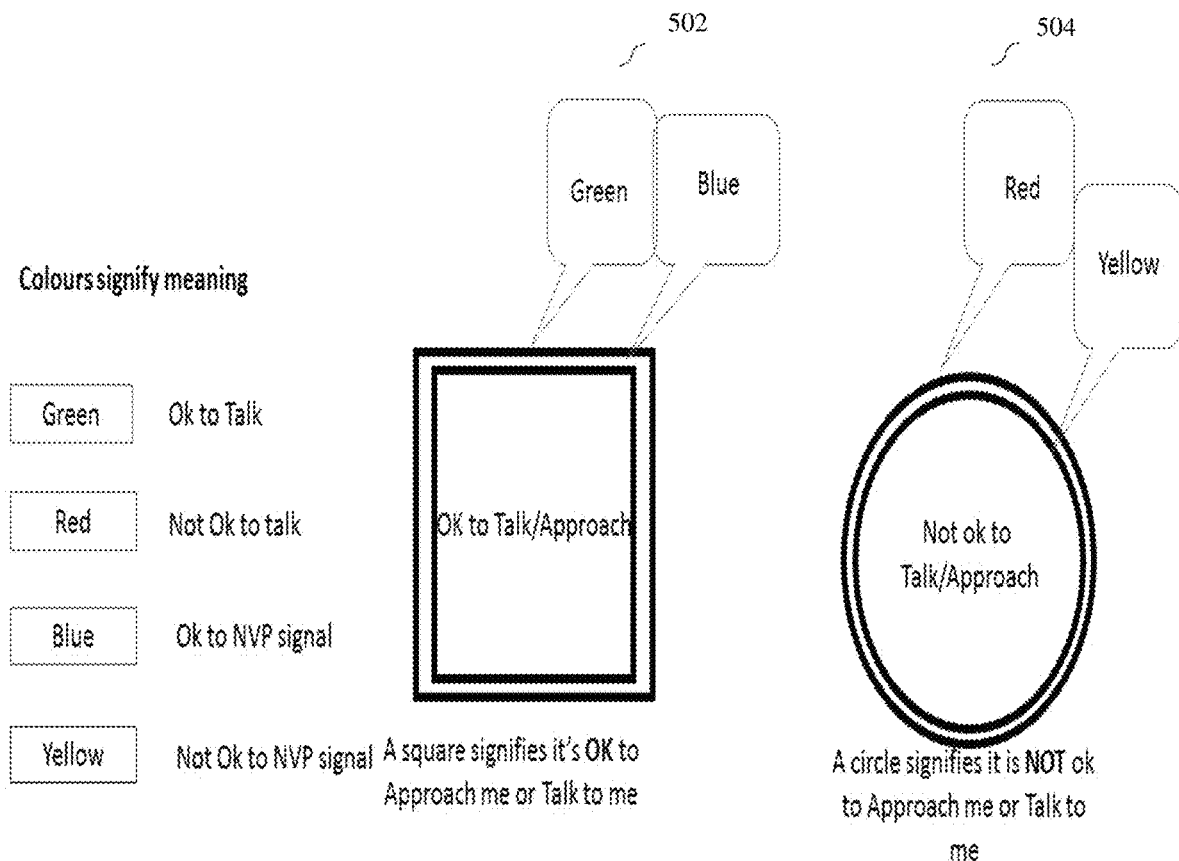
FIG. 5 illustrates a symbol and, or color-coded NVP communication protocol in accordance with an aspect of the invention.

The second component of the NVP is the color of the first component. This color signifies the rules of communication and engagement with the wearer and the receiver. The color signifies whether a person is willing to accept a communication and what type of communication from the viewer. The color can be part of the symbol or a color displayed on or around the badge An example of this is shown in FIG. 5.

Figure 6:
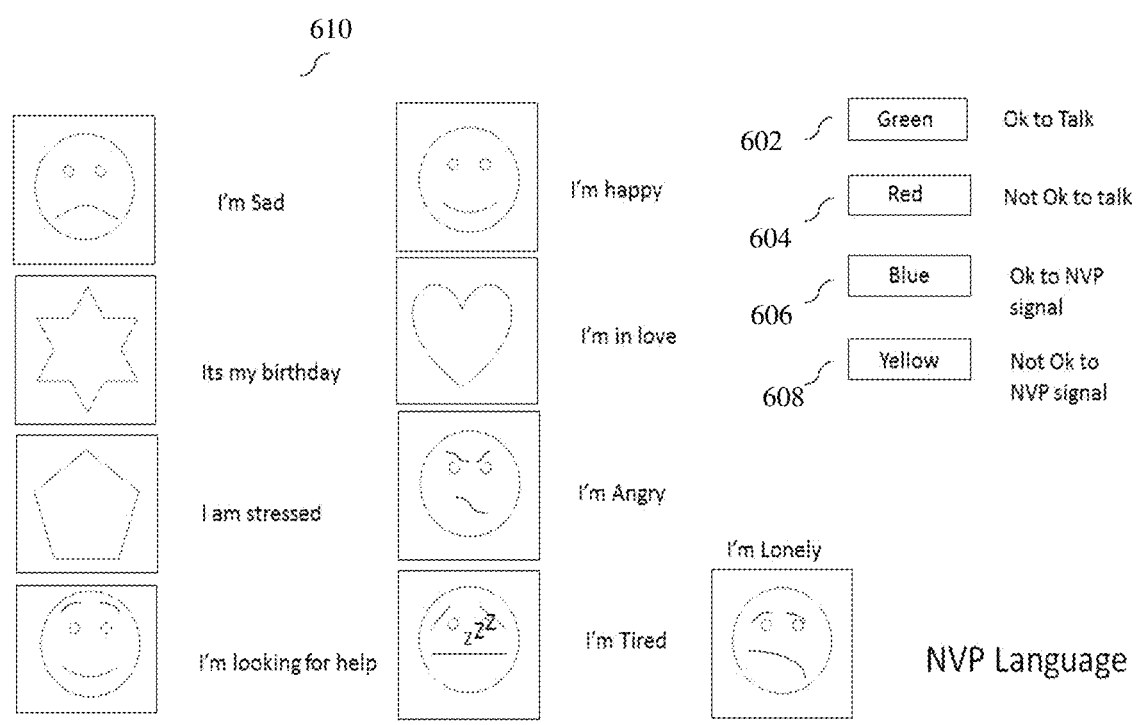
FIG. 6 illustrates a symbol and, or color-coded NVP communication protocol in accordance with an aspect of the invention.

The third component of the NVP is the symbol within the colored shape. These symbols can be anything which conveys a message to the viewer from the wearer but can only be shown using the NVP programming protocol described later. These symbols can be programed to be shown for a certain amount of time using the NVP programming software scheduler and these symbols can also flash based on that scheduler. These symbols can be different colors based on the person's mood. Some examples of the symbols for NVP are shown in FIG. 6.

In a preferred embodiment, disclosed is a non-verbal line of sight electronic communication protocol, the protocol comprising a non-verbal symbol language for communicating wirelessly over electronic devices, including interactive badges and, or displays, between users and, or static receivers, who are in one another's line of sight; and the symbol language displayed on the interactive badge and, or display and, or static receivers communicate whether a first user can approach at least a second user or not for further digital interaction.

For instance, the interactive badge or display that is displaying a blue square 402, 502, 602, which indicates that it's ok to approach me. Inside of which a green square 606 indicates its ok to talk to me and send me a NVP communication and a lonely face 610 from the symbols show that I am lonely. This symbol is programmed to the badge using the NVP programming language software which allows for timing and scheduling. The color of the symbol is the open or closed gateway to the receiver. If the color is not correct the communication will not pass. Alternatively, in other embodiments, any combination of shapes and, or colors may be arbitrarily chosen to signify a permission to approach or activate a further digital content interaction. For instance, a green circle might suggest permission to approach, and a blue square contained therein may suggest a permission to exchange an NVP line of content. Choice of colors, symbols, and the interaction with each, may be purely arbitrary.

The NVP Programming Interface

Figure 7:
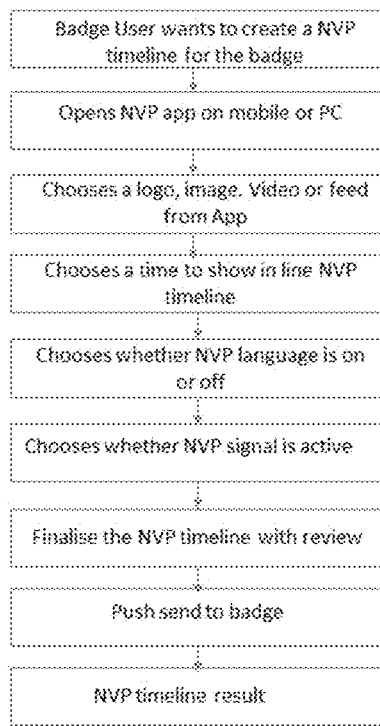
FIG. 7 illustrates an NVP content programming process flow in accordance with an aspect of the invention.
Figure 8:
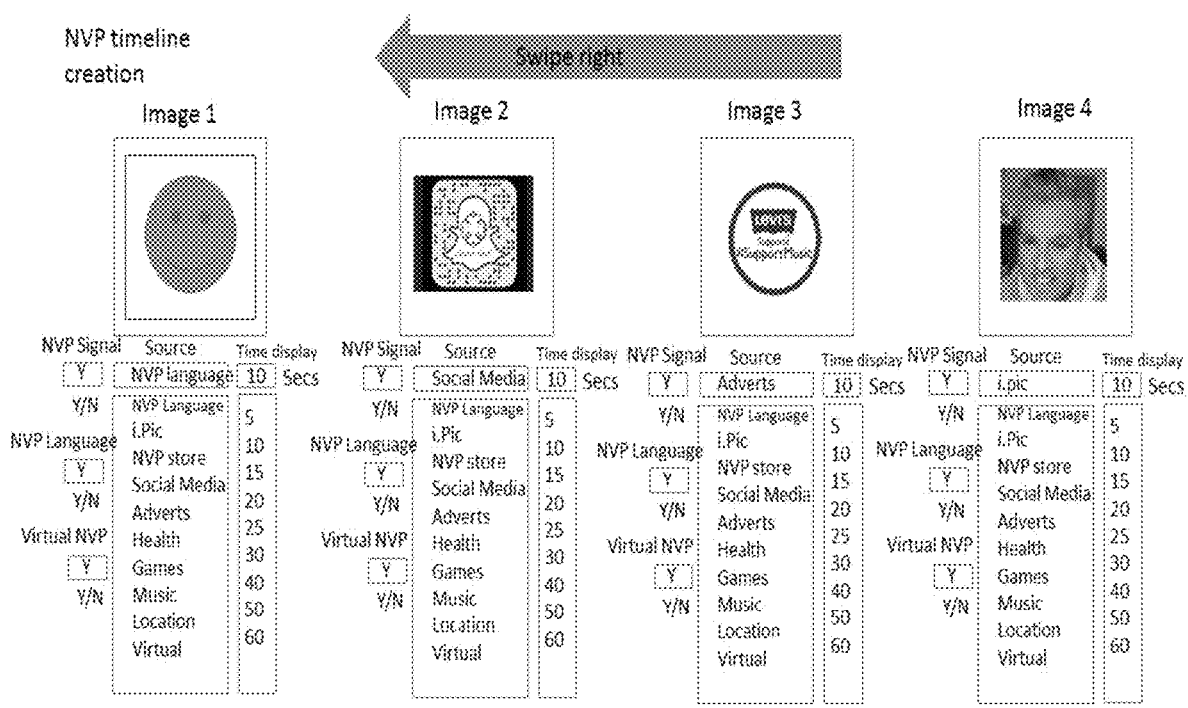
FIG. 8 illustrates a screen shot of a scheduler criteria in accordance with an aspect of the invention.
Figure 9:
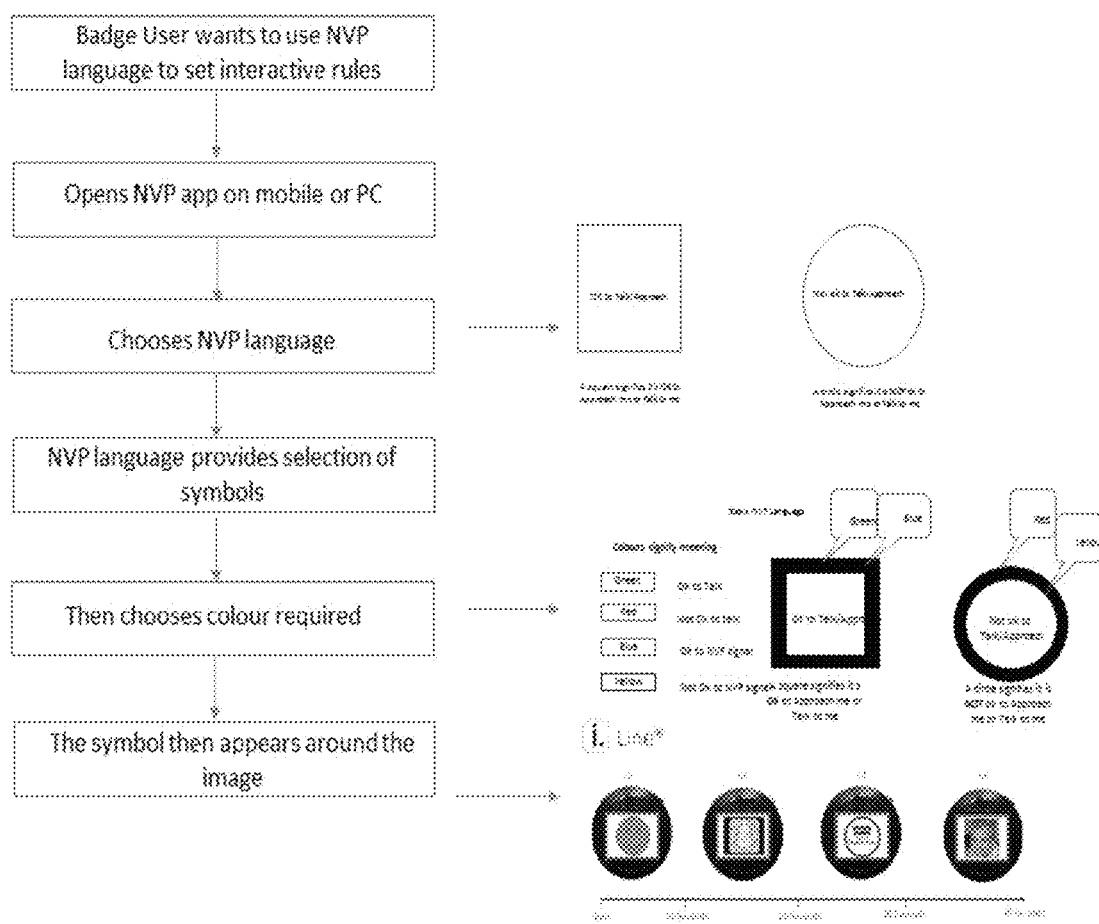
FIG. 9 illustrates an interaction rule process flow in accordance with an aspect of the invention.
Figure 10:
FIG. 10 illustrates a screen-shot of an NVP content display in accordance with an aspect of the invention.

To allow a wearer to program their interactive badge or personal digital display, a programming interface is required which allows the wearer to set up the language on the badge and run it throughout a day as a timeline. This requires a process which is described in detail in FIG. 7. In a preferred embodiment of the process, the wearer decides to program the badge or display with the NVP language; the program which runs on the connected device (smartphone or 10 PC) is opened and the language variables are displayed; the NVP language components 1, 2 and 3 can be selected; the ability to send a communication to another wearer can be selected; and the ability to send the entre NVP wearers timeline can be selected. Additionally, the NVP program allows the wearer to select images from their own images, from the NVP store, feeds from interfaces with social media applications, from adverts selected from the NVP advertising platform, from health devices, from games, music and programming from a specific GPS location. Additionally, the amount of time an image is displayed may be programmed with the resulting timeline transmitted from the device to the wearable badge (FIG. 8). The process for setting the rules of interaction and engagement is further set out in FIG. 9. Once the NVP time line is set, this is transmitted to the badge and can be altered in real time. An example of this in vertical format is shown in FIG. 10. Alternatively, the line of NVP content may be depicted or scrolled in a horizontal fashion.

The NVP Communication Protocol Standard

Figure 11:
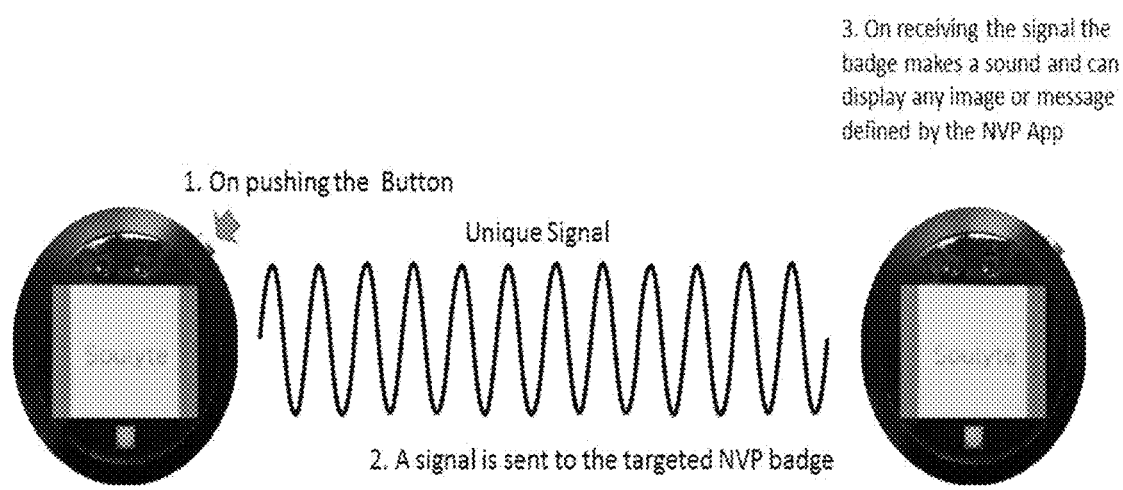
FIG. 11 illustrates a badge-to-badge interaction in accordance with an aspect of the invention.

As illustrated in FIG. 11, the NVP communication system allows one individual who is wearing an interactive badge or screen—in the line of sight of another individual wearing the same—to send messages wirelessly based on the NVP displayed. The message can only be sent if the NVP is set to the correct parameters set out in the NVP language section of this document. The NVP protocol has a unique number attached which allows the receiving interactive badge or screen to decode it and activate an event such as but not limited to an image display, a sound played, a vibration, or a signal sent back to the sender or a signal being sent to the parent smartphone, which in turn activates an event.

This NVP signal is defined as a unique wireless signal sent from one interactive badge or screen to another over a certain physical distance in line of sight. Using the NVP signal, the interactive badge can send an NVP signal to any number of badges or receivers and the badge can accept an NVP signal from any number of badges. The NVP signal can only be accepted if the correct NVP symbols are being displayed. By accepting an NVP signal this can trigger the interactive badge or screen to display anything it's been programmed to by the NVP app running on the smartphone or PC. If accepting the NVP signal this can trigger a sound or vibration or cause a device to trigger a sound or device. On accepting the NVP signal this can trigger the NVP app running on the smartphone to activate an event or process. On accepting the NVP signal, this can trigger the interactive badge or screen via the NVP app to display a set of offers, images, videos or sounds.

In a preferred embodiment, a non-verbal line of sight electronic communication protocol is disclosed, the protocol comprising: a non-verbal symbol language for communicating wirelessly over electronic devices, including an interactive badge with a line of sight device visual display, between users who are in one another's line of sight; the symbol language further comprising a set of any shaped and, or colored symbols that are programmably displayed on the device visual display, wherein the device visual display is at least one of a surround device display and, or a center device display; and based on the programmably displayed set of shaped and, or colored symbols on the device visual display, communicate whether a first user can approach at least a second user or not for further digital interaction.

The technology used to send and receive the NVP signal can be at a specific frequency with a unique number. This has the effect of making any other device not able to recognize the NVP signal or be able to manage the events that have been set by parameters with in the App. This unique number and encryption method makes the NVP interactive badge or screen only recognizable with another NVP interactive badge or screen or receiver or a licensed piece of hardware and software from the NVP group of products. This will be a critical area of protection for the NVP language and protocol—as without it—other manufacturers will not be able to enter the market as people will not be able to interact with their badge. The NVP language is the standard for interactive badges and devices. In short, the NVP signal can be a visual equivalent of a click through.

The Virtual NVP Line

Figure 12:
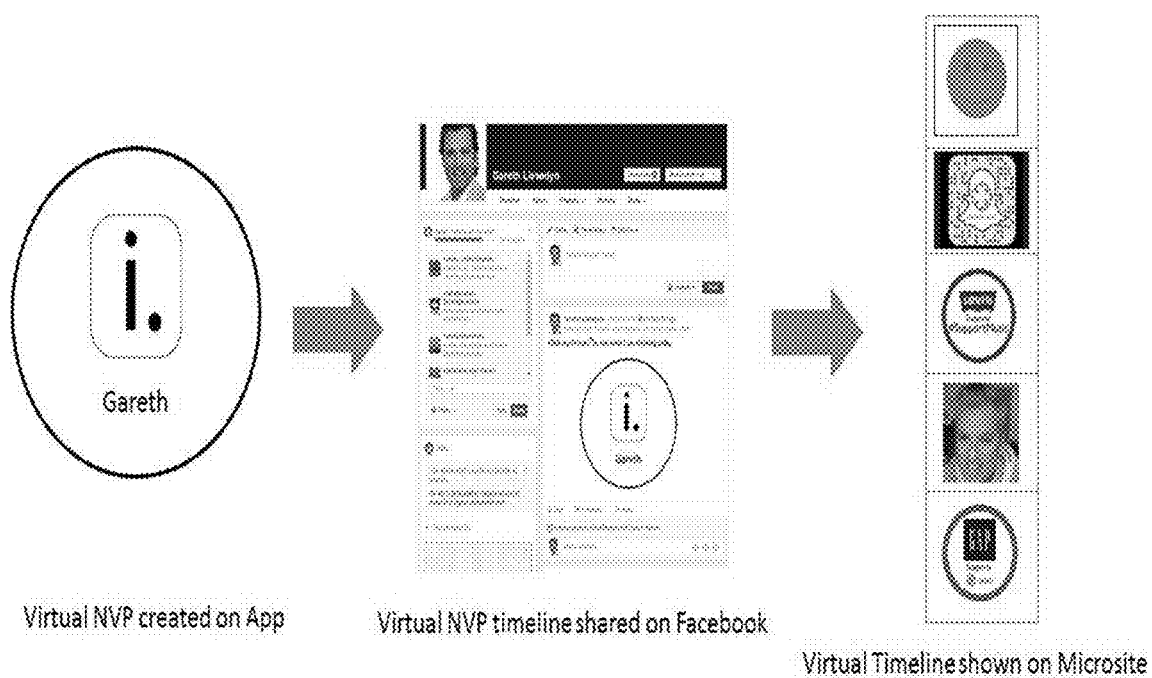
FIG. 12 illustrates an a screen-shot of a virtual NVP timeline in accordance with an aspect of the invention.

FIG. 12 illustrates the transition from badge 1 display; share with badge 2; and digital media share of badge 1 display with tracked footprint (badge 2 share). Virtual NVP is the digital version of the visual NVP line shown on the interactive badge or screen that can be made available to NVP badge users so they can see what others are displaying on their NVP badges that day. There are two uses for the Virtual NVP line: 1) to allow NVP badge wearers to transmit their NVP line from one user to another; and 2) to allow NVP badge wearer to attached their own.

The pre-defined presentation of the content message on at least the interactive device visual display and, or virtual profile may be configured for network or digital sharing. Furthermore, the virtual profile may, via an Application Programming Interface, be configured for transfer and, or further interaction—such as geo-location, site check-in, etc. In other embodiments, the NVP system has been developed so there is a very low entry point for integration to the program. In fact, as the user is only taking a screen shot of their phone for any media there is no integration with 3rd parties necessary. By way of an example, a user could construct a NVP line of their Facebook post, Twitter post, dashboard from Fitbit, images from their phone and a mood image. All of these can be taken directly from screenshots with no outside integration from developers needed. These screen shots can be real time based on the time of NVP line creation.

In some embodiments, live data feeds from monitoring devices would be image related, so rather than display on the device, a mirroring program would allow the device display to be shown on the NVP badge via Bluetooth. This NVP 'Llego' block is a universal interface to all monitoring and real time feed devices.

As each person is responsible for their own NVP line they are responsible for the content that is published. However, the NVP system has a safe guard to ensure that inappropriate and copyright content is not displayed. Each time an NVP line is created it must pass through the NVP 'Llego' Block server to pick up any illegal images. If this happens, the NVP line will be rejected and the user asked to review the images. The NVP 'Llego' block interface allows media channels to display their content on the NVP badge if the user so wishes. These channels are passed through the NVP Llego block centrally and are available for users to connect to if they so wish using the NVP line creation software. There are many markets for the NVP interactive language and its communication protocol. The application that follow are just some examples Application 1:

Advertising Targeting

Figure 14:
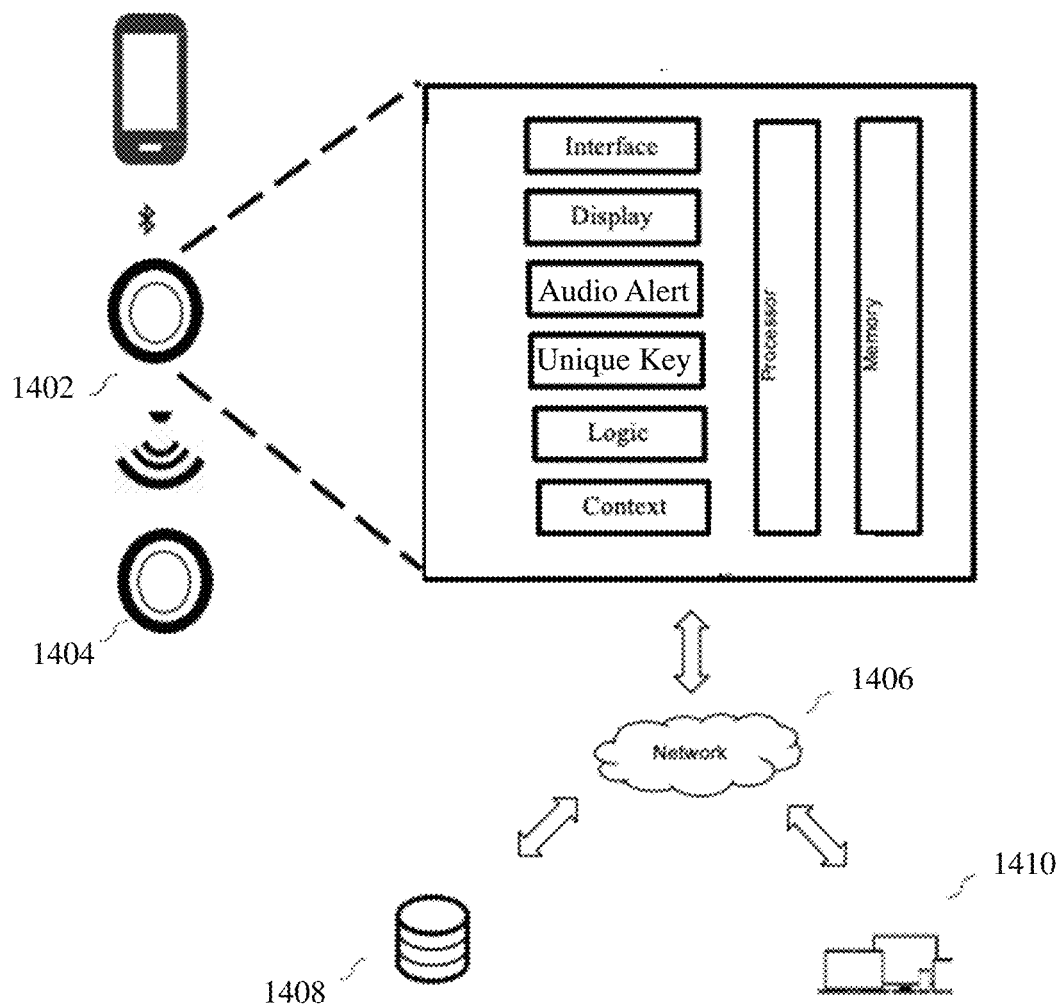
FIG. 14 illustrates a system diagram of the certification and distancing display in accordance with an aspect of the invention.

The groups are based not on where you are digitally i.e. Facebook or Twitter but where you are physically i.e. on a train, at a concert, at a bar or at work. We will be able to count how many NVP signals were sent to individuals and what they reacted to. In this way new physical influencers will emerge, i.e. those who are the most popular. These peoples virtual NVP lines will be the most desirable from an advertising perspective as they will enhance their online profile with that running on their interactive badges or screens. The diagram in FIG. 14 shows what might typically happen to a person wearing and actively using the NVP language on a daily basis.

Figure 13:
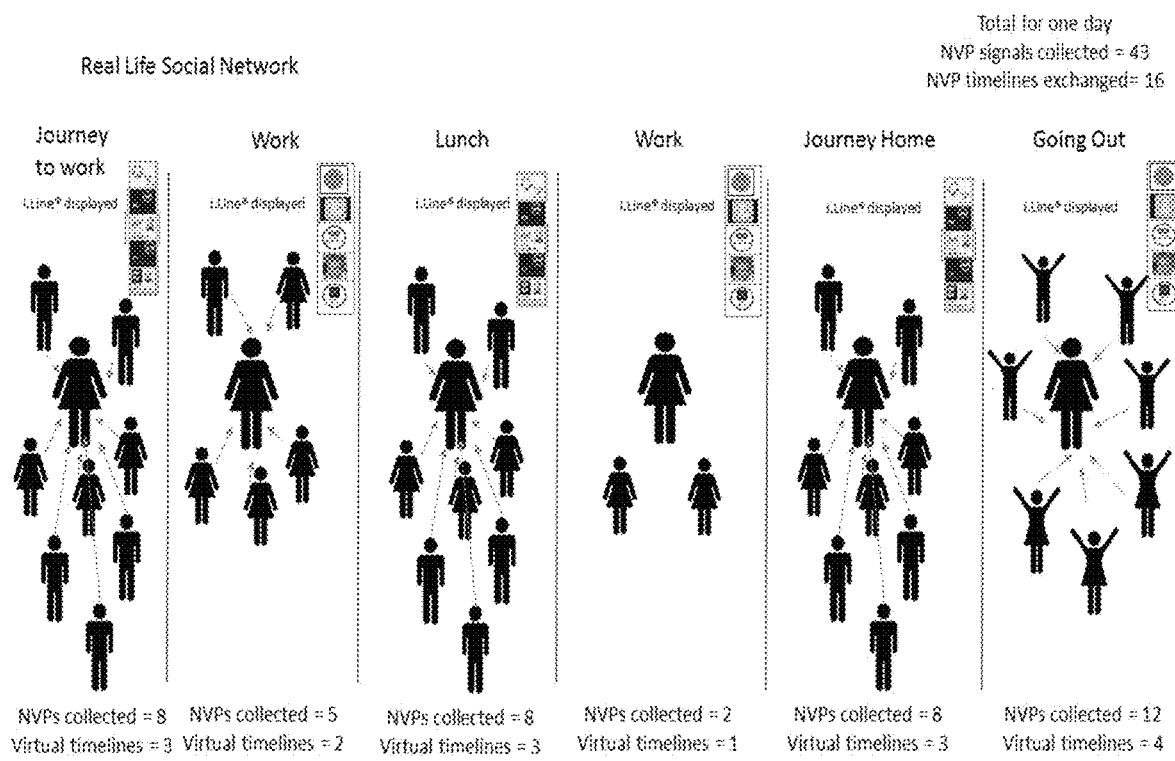
FIG. 13 illustrates an NVP influence map for ad-targeting in accordance with an aspect of the invention.

As illustrated in FIG. 13, girl A has collected 43 NVP signals and had 16 conversations about the NVP line she is displaying. If she has configured her NVP line correctly each person who has sent an NVP signal will have received her Virtual NVP Line. which was reacted to. Note that girl A had configured two NVP lines for different parts of her day. So different people will see different NVP line. What is clear is that as the NVP language and communication protocol becomes established the number of transactions will grow exponentially as each of the above people will have their own NVP badge and their own NVP line We will quickly see the emergence of the top real life influencer in a daily basis. Advertisers will be able to target the most popular real time influencers based on NVP sharing activity.

In other embodiments, the advertising module or platform may further comprise a bidding module, wherein the advertisers bid among each other for engaging a user for incorporating a winning bid advertisement into the content message display of the user. Advertisers will be able to use the NVP Real Time Bidding Network to get access to the NVP line of targeted individuals if they have given their consent to take advertising in their NVP Line. These adverts will be clickable on the Virtual NVP line so they can be transferred from one user to many in the Real Life Network®. This potentially gives advertisers a major new network of people to target based on their location.

Application 2:

The NVP Store or Shop Controlling the NVP Content

Images will be able to be taken from a person's phone and shown on the NVP badge. As these are put onto the NVP line through the NVP App, we have control over the content and can manage any indecent, or inflammatory content. However, the final say will be with the NVP badge wearer. We will have complete control over the Virtual NVP line and be able to stop the distribution of any indecent or inflammatory content. Additionally, there will be a place to purchase widgets that link directly to apps such as Facebook, Twitter and other apps that have integrated with our NVP Llego Block. Brands, Apps and advertiser will have to pay to be allowed on the portal and be subject to our terms and conditions. We expect this fee to be a % of any purchase price or a fixed fee based on an individual's use. i.e. if the wearer wants to buy a specific logo or album cover, they can buy this for a one-off fee from the supplier. We would retain 10% of the retail revenue. This logo would be allowed to be used on the individuals NVP badge, but not be transferrable to another person NVP Line via the virtual NVP line which is read only.

The payment transaction system may incorporate block chain technology, wherein each NVP exchange or digital content purchase transaction among any user is represented as a unique node in the digital ledger, each node tagged with meta data facilitating at least one of a transaction, validation and, or registration for each NVP exchange or digital content purchase transaction. Alternate payment systems may be used, including linking directly to a credit card, debit card, and, or bank account. In yet other embodiments, payment systems may include an intermediary or 3rd party system providing payment processing between users or between user and the NVP store. An intermediary account or escrow-type account may also be used, whereby funds are disbursed from a user 1 account to a user 2 account, or from a user 1-linked intermediary account to a user 2 account—upon full satisfaction of transaction or bidding obligations. The intermediary account may be viewed as a pre-paid account. In other embodiments, digital sellers may target users who have pre-paid an intermediary account for a specific item, thereby competing over a particular purchaser for a specific items.

Moreover, in some embodiments, the NVP communication protocol standard may be incorporated into the payment transaction system coupled to the commerce platform or NVP store. For instance, a yellow square on the surround display or center display of the interactive badge may signify that the user is willing to purchase a digital content for download or a physical item. In other embodiments, the yellow square displayed may signify that after scanning a physical item tag, the user's account or intermediary account has a sufficient balance to afford the item. Contrastingly, a red square may indicate that the item may not be purchased based on available balance. In yet other embodiments, a green circle may signify that a payment transaction is confirmed.

To run through a potential scenario, two individuals have bought an interactive badge which runs the NVP language, communication protocol and programming language. Each one has programmed their badges to run a 6-image timeline changing every 30 seconds. They bothet on a train in the morning and find themselves sitting opposite one another. Individual 1 sees that individual 2 has a green square framing their timeline of images and knows that this signifies that the person is open to a conversation, is open to receiving an NVP signal and is open to receiving a virtual NVP timeline from this person. Individual 1 decides to send a NVP signal which causes the individual 2's badge to display a 'Hi', beep a sounds and flash once as this is standard for the NVP badge.

Individual 1 approaches Individual 2 and starts to discuss their images. Individual 1 also decides to send their virtual NVP timeline to individual 2. At the end of the day Individual 1 and 2 are able to read how many people have sent them a message, from whom and about what. This scenario can happen at any time of the day and the individuals can change the NVP components in real time through their App. Furthermore, individual 1 or 2 can purchase specific digital content from a coupled commerce platform to be displayed on their NVP line or virtual NVP. What's more, advertisers may target either individual 1 and, or 2 for advertising display based on individual 1 and, or 2's tracked activity.

Furthermore, a wide array of other user-initiated transactions may be enabled with use of the interactive badge device. The triggered digital event may further comprise at least one of an offer and acceptance of at least a credit, between at least two devices, redeemable towards at least one of a good or service with any one of a participating vendor. In other embodiments, the triggered digital event further comprises at least one of an offer and acceptance of at least a representation of a good or service, between at least two devices, redeemable towards at least one of a physical good or service associated with the representation from any one of a participating vendor. In other embodiments, the triggered digital event further comprises facilitating a payment transaction between at least one of a device-to-device, device-to-vendor POS terminal, or device-to-vendor product code.

The symbol language further comprises a set of any shaped and, or colored symbols that are displayed on the interactive badge and, or display or foldable display and, or static receivers communicate whether a first user can approach at least a second user or not for further digital interaction. The set of shaped and, or colored symbols that are displayed on the interactive badge and, or display and, or static receivers communicate whether a first user can authenticate the identity of the second user before sending a message. The set of shaped and, or colored symbols that are displayed on the interactive badge and, or display and, or static receivers communicate whether a first user can send a content message to at least a second user or not. Signaling multiple users in a vicinity may be possible, such as a battlefield, convention hall, restaurant, theater, public square, stadium, etc. Also, API-mediated third-party or on-board badge/mobile device sensor-driven contextual information (event type, venue type, weather, attendance, etc.) may factor into the distancing, contact tracing, and/or certification display on the badge device. Display may be on a badge device worn over a user garment in a line-of-sight of another user; badge device affixed to a back surface of a user mobile device; a foldable mobile device co-opted as a badge device with display on the outward-facing (facing another user) screen of the foldable phone. Additionally, an interactive eye-wear may be embedded with a symbol and/or light-display affixed on a frame of the eye-wear and/or lens surface. Much like the interactive badge device, the eye-wear will be paired to a mobile device and operably coupled to a health registry to serve as a public health tool by providing individuals with a line-of-sight distancing/certification display. What's more, a smart watch may be paired with a mobile device and operably coupled to the health registry for distancing/vertification display—though not line-of-sight.

Now in reference to FIG. 14. FIG. 14 illustrates an exemplary system environment in which various embodiments of the distancing and certification line-of-sight device may be practiced. In accordance with an exemplary embodiment, the system may comprise: an interactive badge device with a line of sight device visual display; the device visual display being at least one of a surround device display and, or a center device display; a processor; a non-transitory storage element coupled to the processor; encoded instructions stored in the non-transitory storage element, wherein the encoded instructions when implemented by the processor, configure the system to: upload a decrypted health token from the at least first user-networked device for displaying the "clean" health certification in a form of a color and/or symbol code on the at least first user-worn display device 1402; and upload pre-defined distancing rules from the at least first user-networked device for display on the at least first user-worn display device 1402 of at least one of color/symbol/audio-coded warning of registering presence of at least a second user-worn display device 1404 within a threshold distance of the first user-worn display device 1402 based on the pre-defined distancing rule.

In some embodiments of the badge device 1402, 1404, sensors may be disposed within the device housing, or on the (circular or square) device casing, to capture at least one of a user environmental or contextual data to further inform a user-defined rule. The digital badge device 1402, 1404 communicates with the networked device (mobile communication device) 1410 over a short range wireless communication medium, such as Bluetooth, etc. In other embodiments, sensor input may be derived from devices other than the badge device 1402, 1404. Device input may also encompass the sensor-captured raw data input or transduced and processed data input from any other device associated with the user, such as devices worn, mobile devices, and, or fixed-access devices, such as Internet-of-Things devices (e.g. smart thermostat, home automation consoles, etc.). The plurality of device inputs provides additional input for aggregation and profiling, thus layering additional context for updates to the social distancing rules. For example, in compliance with Center for Disease and Control social distancing guidelines, as a general rule of thumb, people should remain six feet apart from one another. However, this distancing rule may be relaxed if people are engaged in outdoor activities, given the breeze and lack of touching surfaces. This may be especially true if said outdoor activity is jogging on a track, which may have a higher barrier of contagion, compared to waiting on line in a grocery store, for instance, despite the fact that there may be several instances of being within a 6 foot proximity of a fellow jogger. In such instances, the distancing rule may take into account the activity of jogging by input from a fitness band and the fact that the user is jogging outdoors by a geo-location input or badge device sensor input.

While the badge device may be a line-of-sight, body-worn square/circular encasing or housing, any number of form factors may be used to network badge-badge or badge-mobile and perform distancing or certification signaling. While not shown, the badge device may be a wristband, a watch, an armband, a necklace, a headband, a mask, an earring, a waist belt, ring, foldable phone (fold-out/fold-down), detachable display, light or laser-projected onto a screen. Alternatively, the badge device may be any reconfigurable display that may be temporarily or permanently affixed onto a garment of a user. In yet other embodiments, the reconfigurable display may be a flexible OLED tube or screen interwoven into the fabric of the garment, such as a shirt, hat or mask. The symbol and, or color-coded visual display, serving as a vital public health tool by cueing to oneself and others a distancing warning and virus-free certification.

The network 1406 may be any other type of network that is capable of transmitting or receiving data to/from host computers, personal devices, telephones, video/image capturing devices, video/image servers, or any other electronic devices. The network 1406 may be a local, regional, or global communication network, for example, an enterprise telecommunication network, the Internet, a global mobile communication network, or any combination of similar networks. The network 1406 may be a combination of an enterprise network (or the Internet) and a cellular network, in which case, suitable systems and methods are employed to seamlessly communicate between the two networks in a safe manner without compromising sensitive data, such as patient. In such cases, a mobile switching gateway may be utilized to communicate with a computer network gateway of a public health registry to pass data safely between the two networks.

The mobile communication device or networked device 1406 may be paired with a respective digital badge device 1402, 1404 over a short range wireless communication medium. Examples of the short range wireless communication medium include Bluetooth, ZigBee, Infrared, Near Field Communication (NFC) and, or Radio-frequency identification (RFID). Likewise, the digital badge device 1402, 1404 may interact with other digital badge devices 101a, 101b using a short-range communication protocol, such as Infrared, Bluetooth, ZigBee, NFC, and, or RFID.

Preferred embodiments may include the addition of a remote server 1408 or cloud server to further provide for back-end functionality and support. The server 1408 may be situated adjacent or remotely from the system and connected to each system via a communication network 1406. In one embodiment, the server 1408 may be used to support user context (behavior profiling; user history function; predictive learning/analytics; alert function; network sharing function; digital footprint tracking; e-commerce/advertising platform support, etc.). The remote server 1408 may be further configured to authenticate the user and retrieve data of the user, device, and, or network and applies the data against a library of validated user information for enabling a payment or ticket transaction at a fixed-access point deploying an embodiment of the interactive badge device 1402, 1404. More vitally, the server 1408 may be a secured access gateway to sensitive and confidential patient medical data, which may need to be accessed for contact racing purposes or for decryption of a token for "virus-free" certification display.

Figure 15:
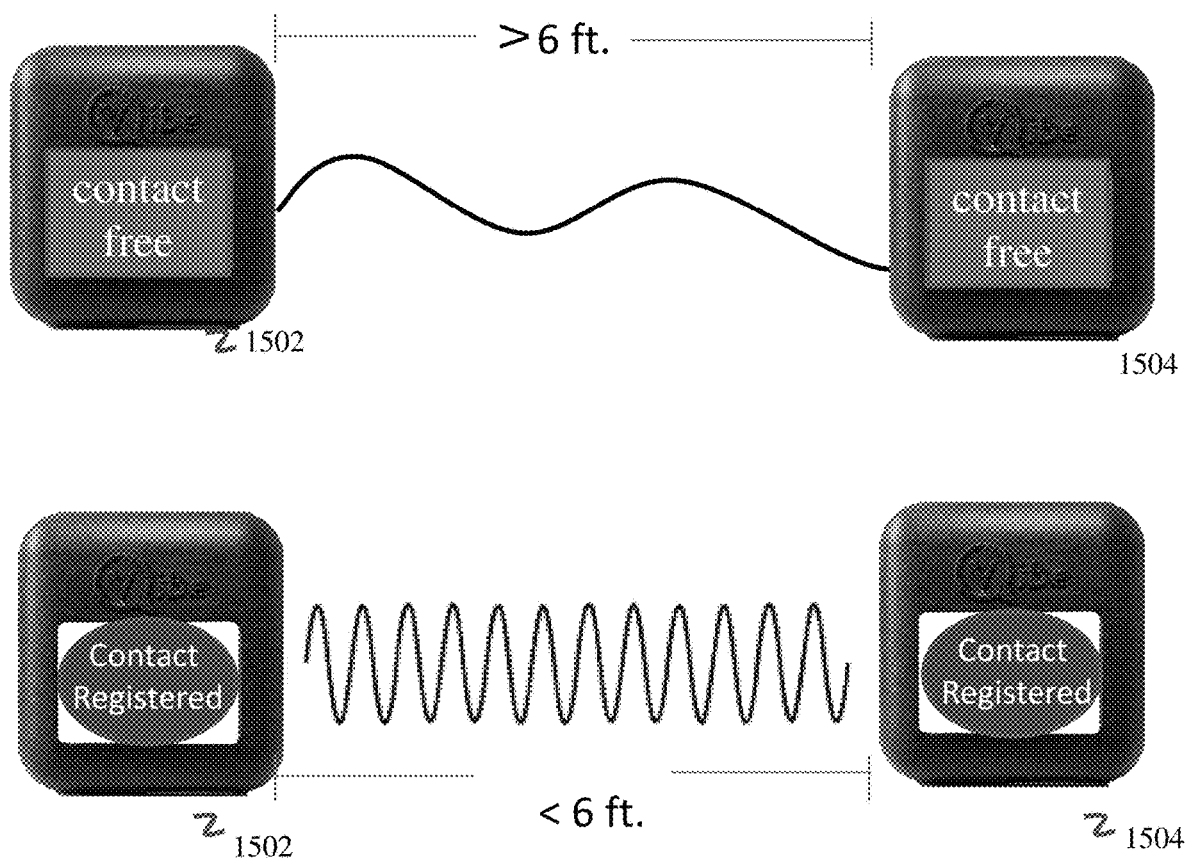
FIG. 15 illustrates an exemplary distancing display scheme in accordance with an aspect of the invention.
Figure 17:
FIG. 17 illustrates an exemplary distancing display legend in accordance with an aspect of the invention.
Figure 17:
Figure 17:
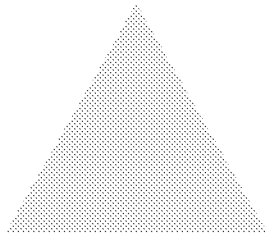
Figure 17:
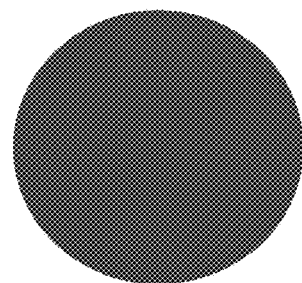

Now in reference to FIGS. 15 and 17, which illustrate an exemplary distancing display schematic and legend, respectively. As shown in FIG. 15, in one embodiment, a first user badge device 1502 may comprise a circular or square housing with center display, further comprising an interface to communicate with a first user networked device and at least a second user badge device 1504. The housing may comprise at least one of a front or side wall with a visual display, wherein said visual display is in a line of sight of at least a second user and displays a symbol or color-coded communication of pre-defined distancing rules. In a preferred embodiment, the first user networked device recognizes the second user networked device within a rule-defined distance by any number of short-range communication. In addition to proximity, the rule may define for duration of contact, whereby only contact above a rule-defined time within proximity is displayed on the line-of-sight badge device display and registered on a public health registry; and contact below the rule-defined time within proximity is simply displayed. As shown in FIG. 17, a green square may indicates contact-free, while a red circle indicates extended contact registered. On the other hand, a red square may indicate a substantial amount of contact, albeit not beyond a pre-defined threshold of time, amounting to an extended contact. Finally, a yellow square may indicate a densely populated area, though no one within a pre-defined proximity to trigger a registered contact. It should be appreciated that the choice of colors and symbol are completely arbitrary. While not shown in FIG. 15, the badge device may be controlled by controls disposed on a side, top, or bottom wall of (circular or square) device casing. In yet other embodiments, the device visual display may be comprised of a dual display: a center device display (shown) and a surround device display, each with similar or unique display capabilities.

In other embodiments, the recognition of a contact-free or registered state may be processed by the line-of-sight badge device in short-range communication with the second user badge device, without pairing involvement from the networked devices. As shown in FIG. 14, the device processor has an interface module or circuitry for interfacing with the first user networked device, a second users badge device, a wider area network to a remote server for analytics and provisioning, or access to a public health registry. Also shown in FIG. 14, is a wide array of other processing capabilities that may be performed by the badge device alone, or in combination with the networked device—amounting to off-loading processing throughput from the networked device to the badge device.

In one embodiment, contact registering may further comprise (1) being within a wireless communication short-range of the at least second user-worn display device; (2) transmitting a signal with a tag to the at least second user-worn display device; (3) accepting the signal with the tag by the at least second user-worn display device; (4) decoding the tag by the at least second user-worn display device to trigger a digital event comprising at least one of a sound, vibration, flash, signal, symbol, color, text, curated line of static, dynamic or scheduled images or video content for display or download on the first and at least second user display device, or for upload over a network, wherein said digital event marks exceeding a threshold distance based on the pre-defined distancing rule.

The determination of contact and the extent of contact may be based on a signal strength of short-range communication. In other words, a signal recognized beyond a threshold strength may signify a threshold proximity. A threshold signal may be further characterized to fall within a spectrum of strength—corresponding to a spectrum of proximity; the weaker the threshold signal, the less substantial the registered contact. While it is not reflected in the legend illustrated in FIG. 17, a wider assortment of colors and symbols may be incorporated in order to reflect the extent of how substantial the registered contact is. Again, this may be distinguished from an extended contact (red circle FIG. 17), which is deduced from a time function—in addition to proximity—and is undoubtedly a more probative indicator of infection propensity.

Furthermore, inter-device interaction for achieving distancing display/warning may comprise a wireless signal sent from one user to at least one of a second user, group of users, venue entry (VE) terminal, Point-of-Health Certification (POHC) terminal, gate-keeper scanner, or static receivers, which transfers data based on the shaped and/or colored set of symbols displayed on at least one of a user's display device or static receivers. The data transferred may be primary information displayed on the badge device display in the form of color and/or symbols to convey a distancing or health status message. Alternatively, a secondary line of information may be displayed detailing time of registered contact information, date of health status certification issued from a health registry, duration of contact, extent of contact (at least one of substantial or non-substantial), etc.

In addition to contact alerting to ensure safe distancing, contact tracing is a critical public health tool for containing any infectious outbreak. Contact tracing is defined as the process of identification of persons who may have come into contact with an infected person ("contacts") and subsequent collection of further information about these contacts. By tracing the contacts of infected individuals, testing them for infection, treating the infected and tracing their contacts in turn, public health may aim to reduce infections in the population. On a high level, there are three major levels to contact tracing:

Contact identification: Once someone is confirmed as infected with a virus, contacts are identified by asking about the person's activities and the activities and roles of the people around them since onset of illness. Contacts can be anyone who has been in contact with an infected person: family members, work colleagues, friends, or health care providers.

Contact listing: All persons considered to have contact with the infected person should be listed as contacts. Efforts should be made to identify every listed contact and to inform them of their contact status, what it means, the actions that will follow, and the importance of receiving early care if they develop symptoms. Contacts should also be provided with information about prevention of the disease. In some cases, quarantine or isolation is required for high-risk contacts, either at home, or in hospital. Contact follow-up: Regular follow-up should be conducted with all contacts to monitor for symptoms and test for signs of infection.

(World Health Organization) The exercise of Contact Listing may be exponentially expedited by having the badge device be in communication with a public health registry. The registry may keep a running tabulation of badge device identifiers, and for each badge device, a running list of registered contacts identified by badge device identifier.

Figure 19:
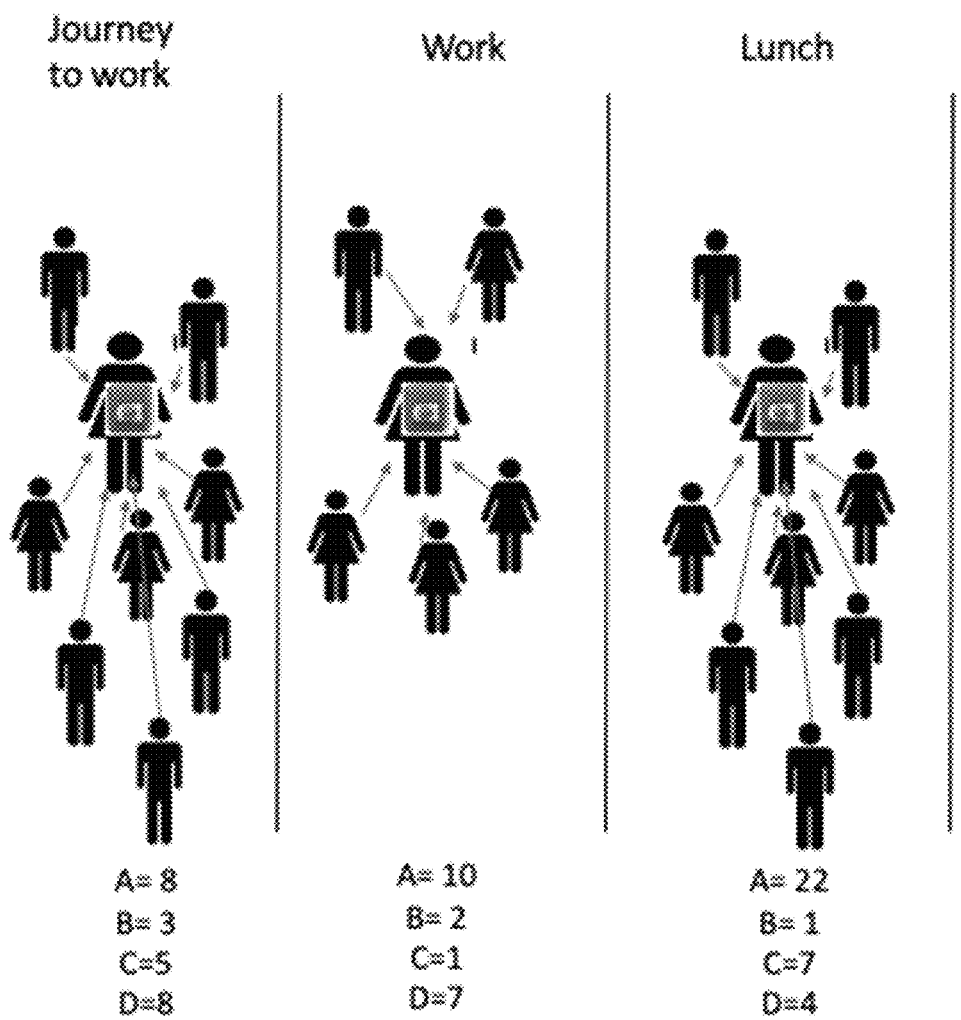
FIG. 19 illustrates an exemplary contact tracing diagram in accordance with an aspect of the invention.

As shown in FIG. 19, illustrating a contact tracing scheme in accordance with an aspect of the invention, the system and/or registry-maintained database keeps a running tab on registered contacts for user. It is organized in terms of time period, and the number of registered contacts during each time period in terms of their health status (A—Had infection, has antibodies; B—Infection-free; C—Not been tested; and D—Vaccinated). For instance, as illustrated in FIG. 19, user registered 13 contacts with individuals not yet tested during the course of his/her commute to work and up until lunch (C=5+C=1+C=7). Once a registered contact is confirmed positive for an infectious disease, he or she may be asked to voluntarily or mandatorily report the results to the public health registry, and the registry may communicate to all registered contacts of the infected that have been exposed and begin to prompt an isolation instructional. Beyond just communicating the fact that registered contacts of an infected may be exposed, other details may be provided, such as time of exposure and extent of exposure (contact, extended contact, extended contact grade 1, extended contact grade 2, substantial contact, substantial contact grade 1, substantial contact grade 2, etc.). This line of communication may be expressed in symbol and/or color code consistent with the legend displayed in FIG. 17. In one embodiment, the badge device system database and/or public health registry-maintained database of user-worn display device identifiers with a real-time contact trail for each user (identified by an identifier) may be coupled to the at least first user device (mobile/badge) via a network for informing the entire contact trail of any user confirmed positive (self-reported or registry reported). Informing each user of the contact trail may further comprise at least one of the following information: date of contact with positively confirmed user; time of contact; location of contact; extent of contact, duration of contact; environmental information; or context of contact.

Figure 16:
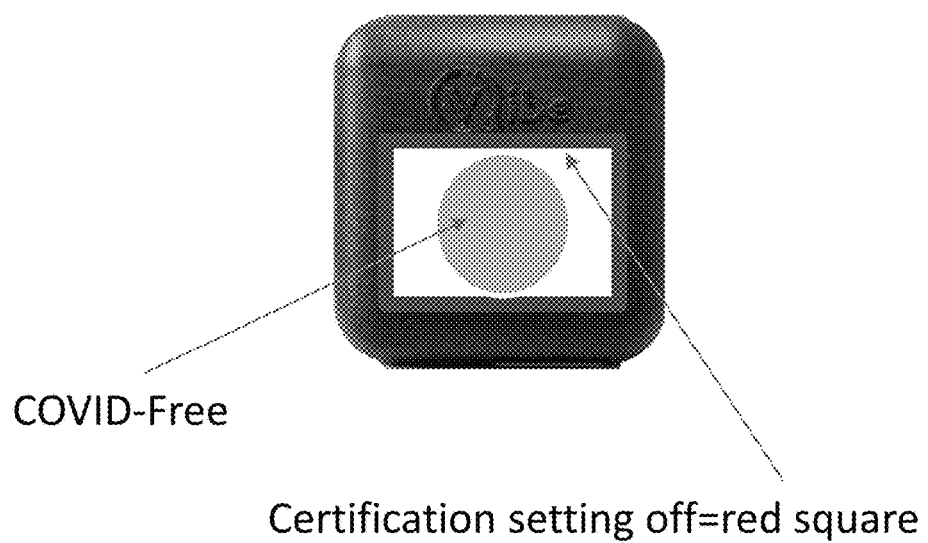
FIG. 16 illustrates an exemplary certification display scheme in accordance with an aspect of the invention.
Figure 16:
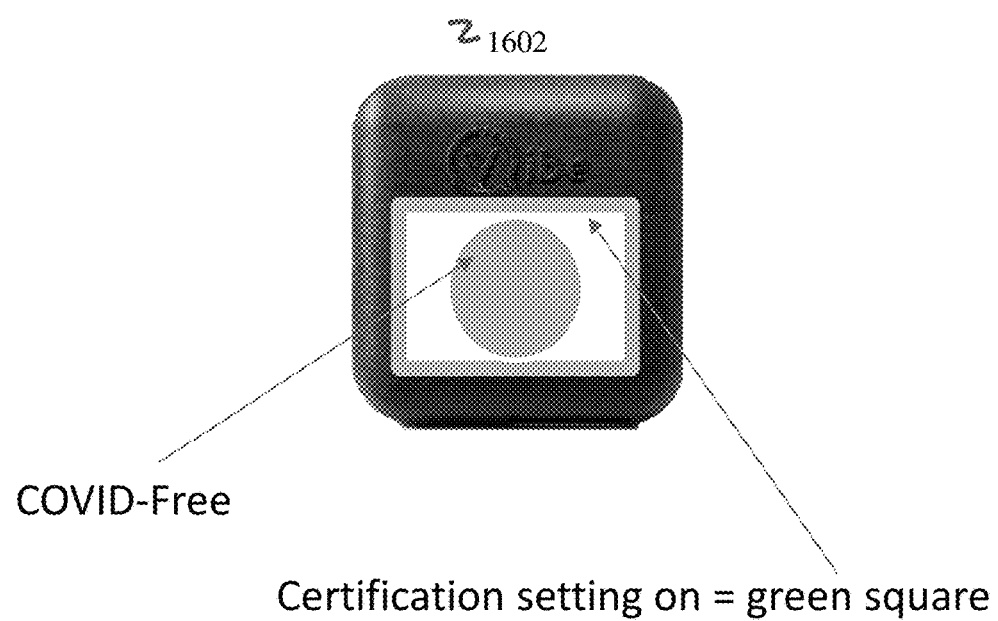
Figure 18:
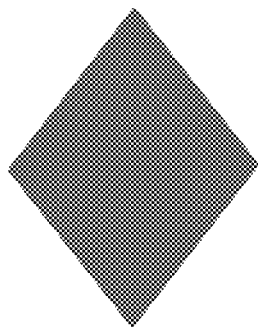
FIG. 18 illustrates an exemplary certification display legend in accordance with an aspect of the invention.
Figure 18:
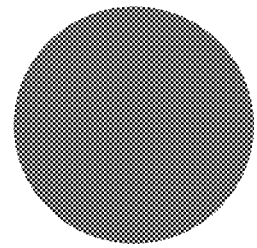
Figure 18:
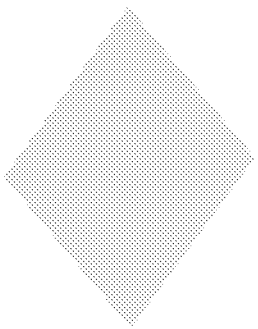
Figure 18:
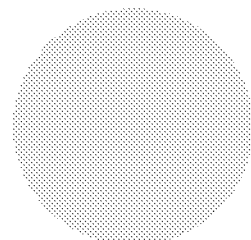

Now in reference to FIGS. 16 and 18, illustrating an exemplary certification display scheme and legend in accordance with an aspect of the invention, respectively. As shown in FIG. 16, the interactive, line-of-sight badge device may be communicatively coupled to a remote public health registry and decrypt/display a real-time "Covid-Free" certification (indicated by a green circle surrounded by a green square) for the user. This would allow "gate-keepers" of institutions to rest assure of the users admission. The user would have an option to opt-out of the "real-time" check and display a green circle surrounded by a red square—indicating a "Covid-Free" certification, albeit not real-time, though within a pre-defined period of time. As shown in FIG. 18, other potential display scenarios may be a green diamond indicating "Covid-Free", however, untested within the last two weeks; a yellow circle indicating "Vaccinated" within the last 12 months; and a yellow diamond indicating "Vaccinated" outside of the 12 month window. It should be appreciated that any choice or combination of colors, shapes, and pre-defined windows of time may be used for the certification display. With that said, the selection will need to be universalized among users to convey an unambiguous signal to at least one of: Other users, fixed-access terminals (VE/POHC), or "gate-keepers".

In another potential exemplary display and interaction scheme: When the receiving users device reads these symbols or rules it changes the status of its own badge to reflect whether that person can enter a location or space around the badge. In another potential exemplary display legend: Antibody present in the user and not able infect—Safe—green square; Had the COVID 19 virus and therefore unlikely to be carrying—Safe—yellow Square; Not had the COVID 19 virus—warning—purple; Has the COVID 19 virus—Unsafe—red, or (A) Had infection; has antibodies (green square); (B) Infection-Free (green circle); (C) Not been tested; (D) Vaccinated.

Any number of color and symbol choices may be displayed for signaling at least one of the above four health status, vis-à-vis, a viral state (Covid-19, for instance). In addition to color and symbol language, any configuration of audio, flash, or vibrational alerts may be deployed on the user device (badge/mobile). The interactive nature of the badge is the most critical aspect of this public health tool. In some embodiments, if a badge comes within a distance of another, while displaying a noncompatible color/symbol, at least one of the two interacting badges may at least one of color/symbol display, flash, vibrate, or be audible. This alert output will serve three purposes: To inform others around of the status (clean/not clean) and permission to approach; To allow or block people interacting digitally with the user; To allow (clean) user to enter physical locations.

In other embodiments, only similar (or compatible) signal display on each interactive badge device will trigger a further digital event. Digital events may be a transaction of any kind, information exchange, social media exchange, public heath registry requests/verification, etc. Conversely, dissimilar display between interactive badges will not trigger a digital event between badges/users.

Figure 20:
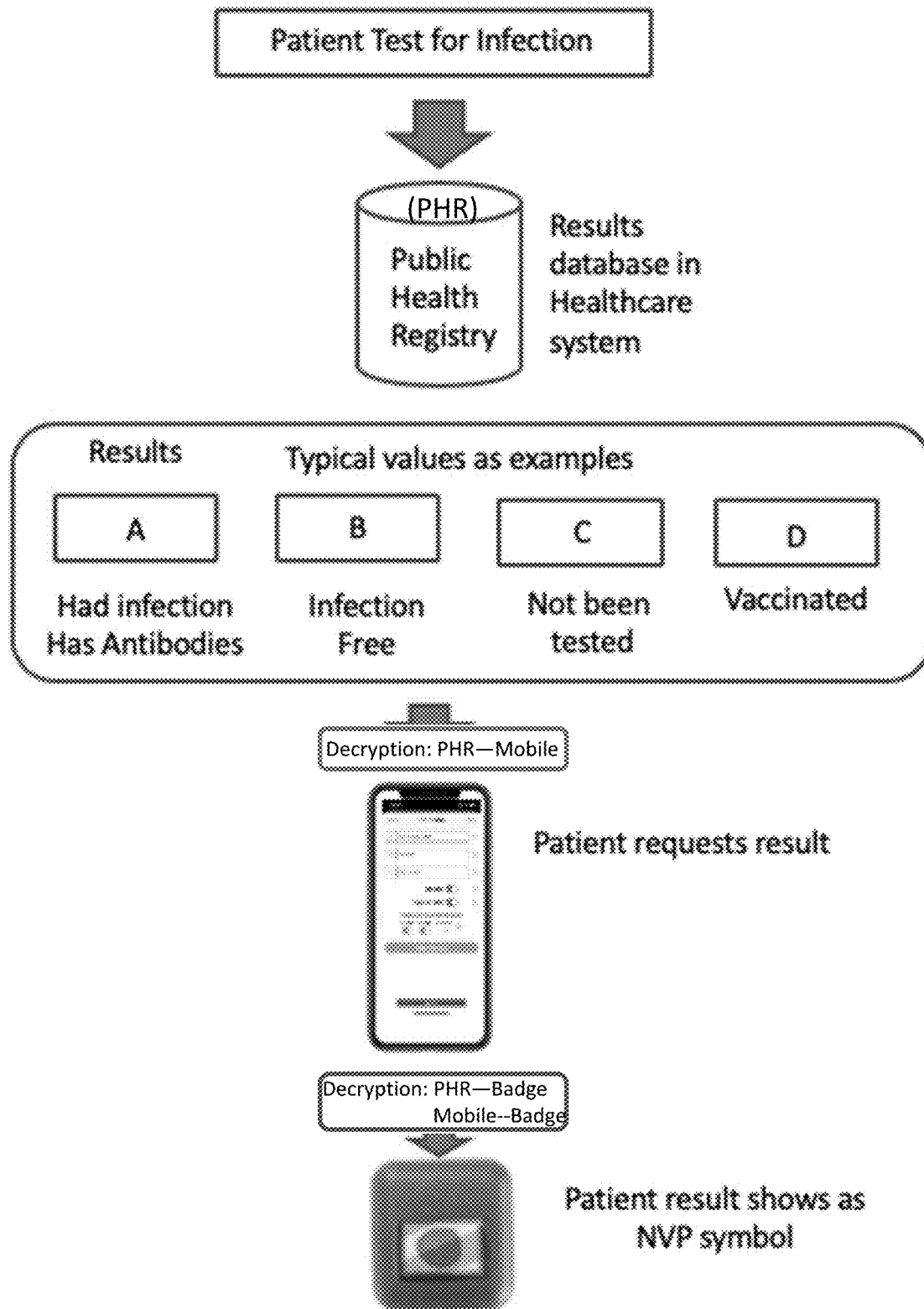
FIG. 20 illustrates an exemplary decryption/display pathway in accordance with an aspect of the invention.
Figure 21:
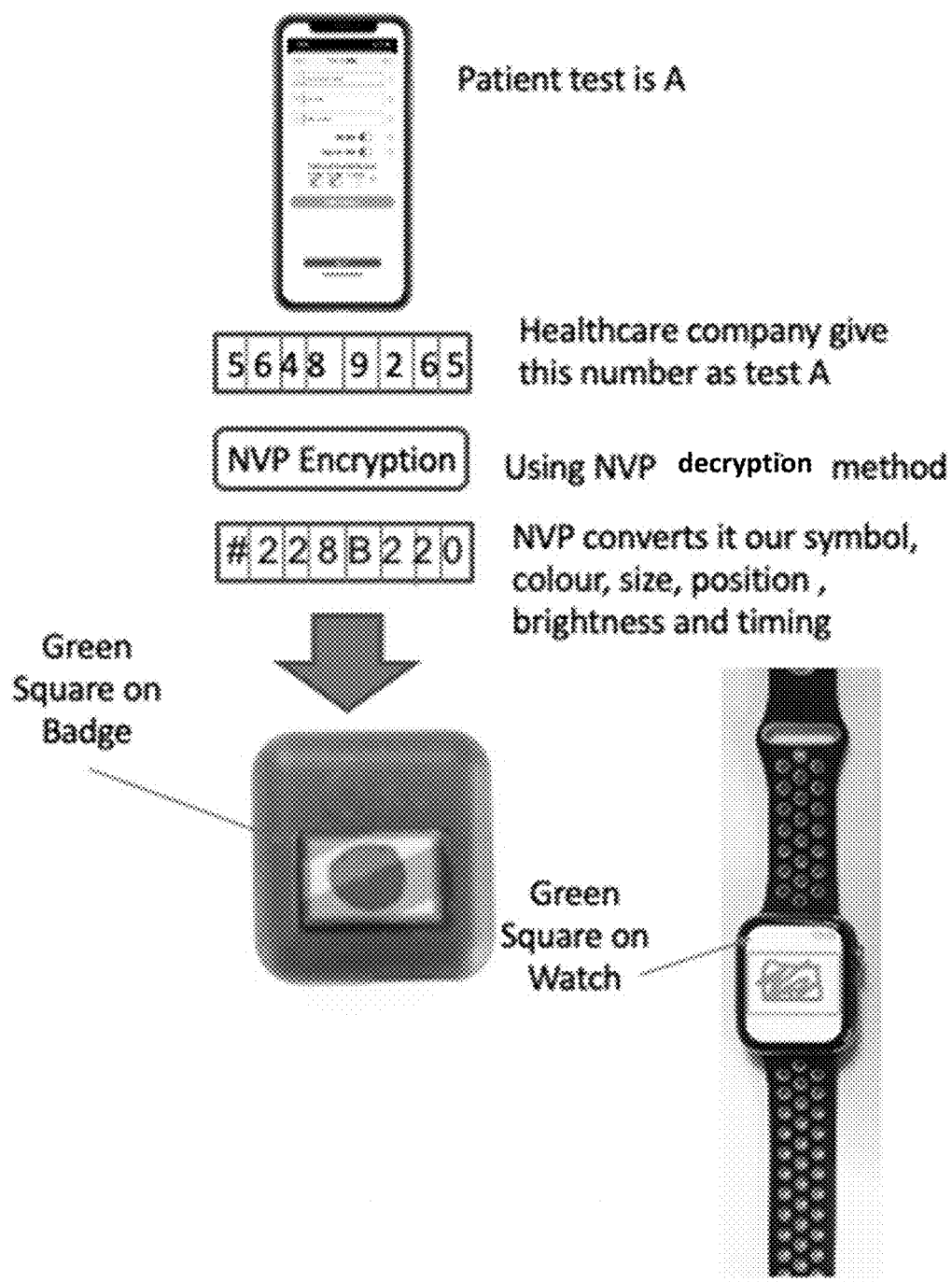
FIG. 21 illustrates an exemplary method flow diagram of the steps involved in achieving the distancing/certification display in accordance with an aspect of the invention.

Privacy of the users identity and sensitive medical information is of utmost importance. It is critical that the operably coupled badge device is not susceptible to security breaches—either at the device level, intermediary points, or public health registry level. Users may be masked by a badge identifier and test results may be packaged in encrypted packet/s (token). Each badge device may comprise a key unique to the badge identifier and token for downstream decryption and eventual display. This decryption/display pathway (as illustrated in FIGS. 20 and 21) is just one of many potential safe-packet-transfer mechanisms among any number of nodes in the network. In other embodiments, an enhanced packet transfer logic or other safe transfer enhancements may further be embedded in every node/network that further allows safe packet transfer between independent nodes without loss, corruption, or denial-of-service related events. For instance, in some embodiments, a packet seal (cryptographic identifier) may be comprised within the packet. In other embodiments, safe transfer enhancements may include a public key identifier to locate and verify any sending or receiving node in any given transfer scheme. In another embodiment, a transfer scheme may further comprise the step of supplying a signed receipt of at least one of a successful packet receipt or transfer from at least a first node to at least a second node. The receipt comprising at least one of a public key or packet seal from a receiving node, combined with a cryptographic hash of the sending node. For instance, end node (user mobile device or interactive badge device) will supply signed receipt for encrypted packet (health status certification) received from public health registry, instead of just a success message. It's cryptographic hash of device identified token from the registry node combined with user device public key. This signature proves that the correctly requesting user device node successfully received the encrypted certificate for decryption and display and that it is in fact the correct end user device, defined by identifier, which received it.

In other embodiments, the unlocked/decrypted health certificate may be in a stealth mode, whereby the certificate is not line-of-sight displayed on the interactive badge device display, but rather, the certificate may be verified by a close-range interaction between "gate-keeper" interactive badge device and user badge/mobile device. Alternatively, the "gate-keeper" may close-range interact with the user device (badge/mobile) via an independent scanner operably coupled to a remote server (system/registry). In yet other embodiments, a badge device may be scanned by a VE/POHC fixed-access terminal for health status verification, despite not displaying a color/symbol code due to being in a "stealth" state.

FIG. 22 illustrates an exemplary method flow diagram for certification and distancing display on a user-worn badge device for infection prevention in accordance with an aspect of the invention. Step 1 entails: uploading a decrypted health token from the at least first user-networked device for displaying the "clean" health certification in a form of a color and/or symbol code on the at least first user-worn badge device 2202; and step 2 entails uploading a pre-defined distancing rules for displaying at least one of color/symbol/audio-coded warning of registering presence at least a second user-worn badge device within a threshold distance of the first user-worn badge device based on the pre-defined distancing rule 2204.

In other embodiments, the badge device exclusively deploys distancing waning/contact tracing, while not certifying a "clean" health status. The method for communicating pre-defined distancing rules on a user-worn badge display may comprise the steps of: programming a first badge device to alert upon recognizing another badge device based on a pre-defined rule, wherein the pre-defined rule factors at least one of: a wireless network strength, location, environment, activity, age of at least one of the users, pre-existing health of at least one of the users, or infection status of at least one of the users; and outputting an alert from at least the first badge device, wherein the alert is at least one of an audible output, flash, vibration, or color/symbol display.

In other embodiments, the badge device exclusively deploys a health status certification, while not deploying distance warning. The method for signaling a health registry-issued certificate on a user-worn badge display may comprise the steps of: coupling a user mobile device or badge device to a health registry for real-time decryption of a health registry-issued health certificate over a network; and outputting a color/symbol-coded display on the user badge device of a user health status based on the real-time decrypted health certificate.

Embodiments are described at least in part herein with reference to flowchart illustrations and/or block diagrams of methods, systems, and computer program products and data structures according to embodiments of the disclosure. It will be understood that each block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

I claim:

1. A system comprising:
   a first user badge device;
   a first user mobile device;
   a second user badge device:
   said first user badge device housing an interface to communicate with at least the first user mobile device and the second user badge device;
   a network;
   a processor, non-transitory storage element coupled to the processor, and encoded instructions stored in the non-transitory storage element, wherein the encoded instructions when implemented by the processor, configure the first user badge device to:
     receive/upload a decrypted health token associated with a first user from the first user mobile device through short-range wireless communication;
     display a symbol and color-code related to a vaccination status of the first user in response to the received/uploaded decrypted health token;
     transmit a signal along with data to the second user badge device, wherein the data contains the symbol and color-code to convey a vaccination status;
   a processor, non-transitory storage element coupled to the processor, and encoded instructions stored in the non-transitory storage element, wherein the encoded instructions when implemented by the processor configure the second user badge device to:
     receive the signal from the first user badge device through the short-range wireless communication; and
     display the symbol and color-code related to the vaccination status of the first user on the second user badge device, wherein the symbol and color code signals/validates safe entry of the first user to enter a premise.

2. The system of claim 1, wherein the vaccination status is displayed on any one of a second user device for scanning, or a fixed access terminal by: (1) being within a wireless communication short-range of the first user badge device or first user mobile device; (2) transmitting a signal with a tag to any one of the second user device for scanning or fixed access terminal; (3) accepting the signal with the tag by any one of the second user device for scanning or fixed access terminal; (4) decoding the tag by any one of the second user device for scanning or fixed access terminal to trigger a digital event comprising at least one of as sound, vibration, flash, signal, symbol, color, text, curated line of static, dynamic or scheduled images or video content for certification display of the first user's vaccination status on any one of the second user device for scanning or fixed access terminal.

3. The system of claim 1, further comprising a wireless signal sent from a first user to at least one of a second user, group of users, fixed-access terminal, or static receivers, which transfers data for decoding to validate the vaccination status of the first user, wherein the validation is in the form of a color and/or symbol coded display on any one of the second user's badge device, group of users badge devices, or fixed-access terminal.

4. The system of claim 2, wherein the tag is decoded by a fixed access terminal validating at least the first user associated with the first user badge device or first user mobile device transmitting the signal comprising said tag.

5. The system of claim 4, wherein the fixed access point is a Point of Health Check (POHC) terminal at an entry of any one of a public venue.

6. The system of claim 1, wherein at least the first user badge device is secured on a first user or on a back wall of the first user mobile device for achieving line-of-sight display.

* * * * *